US012171872B2

(12) United States Patent
Holton, Jr. et al.

(10) Patent No.: US 12,171,872 B2
(45) Date of Patent: *Dec. 24, 2024

(54) ORAL COMPOSITIONS AND METHODS OF MANUFACTURE

(71) Applicant: NICOVENTURES TRADING LIMITED, London (GB)

(72) Inventors: Darrell Eugene Holton, Jr., Clemmons, NC (US); Ronald K. Hutchens, East Bend, NC (US); Jeremy Barrett Mabe, Lexington, NC (US); Kristen Ann Spielbauer, Kernersville, NC (US); Matthew Evan Lampe, Winston-Salem, NC (US); Ross Jay Oden, Winston-Salem, NC (US); Michael Andrew Zawadzki, Clemmons, NC (US); Anthony Richard Gerardi, Winston-Salem, NC (US)

(73) Assignee: NICOVENTURES TRADING LIMITED, London (GB)

( * ) Notice: Subject to any disclaimer, the term of this patent is extended or adjusted under 35 U.S.C. 154(b) by 790 days.

This patent is subject to a terminal disclaimer.

(21) Appl. No.: 17/164,950

(22) Filed: Feb. 2, 2021

(65) Prior Publication Data

US 2021/0169792 A1 Jun. 10, 2021

Related U.S. Application Data

(63) Continuation of application No. PCT/IB2020/061473, filed on Dec. 4, 2020, and a continuation-in-part of application No. 16/707,343, filed on Dec. 9, 2019, now Pat. No. 11,883,527.

(60) Provisional application No. 63/036,127, filed on Jun. 8, 2020.

(51) Int. Cl.
| | |
|---|---|
| A61K 9/00 | (2006.01) |
| A61K 31/131 | (2006.01) |
| A61K 31/198 | (2006.01) |
| A61K 31/375 | (2006.01) |
| A61K 31/4415 | (2006.01) |
| A61K 31/522 | (2006.01) |
| A61K 31/714 | (2006.01) |
| A61K 36/752 | (2006.01) |
| A61K 47/02 | (2006.01) |
| A61K 47/10 | (2017.01) |
| A61K 47/26 | (2006.01) |
| A61K 47/36 | (2006.01) |
| A61K 47/46 | (2006.01) |

(52) U.S. Cl.
CPC .......... *A61K 9/0056* (2013.01); *A61K 31/131* (2013.01); *A61K 31/198* (2013.01); *A61K 31/375* (2013.01); *A61K 31/4415* (2013.01); *A61K 31/522* (2013.01); *A61K 31/714* (2013.01); *A61K 36/752* (2013.01); *A61K 47/02* (2013.01); *A61K 47/10* (2013.01); *A61K 47/26* (2013.01); *A61K 47/36* (2013.01); *A61K 47/46* (2013.01)

(58) Field of Classification Search
CPC .. A61K 9/0056; A61K 36/752; A61K 31/131; A61K 31/198; A61K 31/375; A61K 31/4415; A61K 31/522; A61K 31/714; A61K 47/02; A61K 47/10; A61K 47/26; A61K 47/36; A61K 47/46
See application file for complete search history.

(56) References Cited

U.S. PATENT DOCUMENTS

| | | | |
|---|---|---|---|
| 4,997,654 | A | 3/1991 | Corsello et al. |
| 5,417,229 | A | 5/1995 | Summers et al. |
| 6,138,683 | A | 10/2000 | Hersh et al. |
| 6,845,777 | B2 | 1/2005 | Pera |
| 6,958,143 | B2 | 10/2005 | Choi et al. |
| 7,032,601 | B2 | 4/2006 | Atchley et al. |
| 7,056,541 | B1 | 6/2006 | Stahl et al. |
| 7,507,427 | B2 | 3/2009 | Andersen et al. |
| 7,810,507 | B2 | 10/2010 | Dube et al. |
| 7,833,555 | B2 | 11/2010 | Andersen et al. |
| 7,861,728 | B2 | 1/2011 | Holton, Jr. et al. |

(Continued)

FOREIGN PATENT DOCUMENTS

| | | |
|---|---|---|
| CN | 103005680 | 4/2013 |
| CN | 103263507 | 8/2013 |

(Continued)

OTHER PUBLICATIONS

Robichaud Meagan et al., "Tobacco companies introduce 'tobacco free' nicotine pouches", *Tob Control 2019*, Nov. 21, 2019, 1-2, National Library of Medicine, doi:10.1136/tobaccocontrol-2019-055321.

(Continued)

*Primary Examiner* — Blessing M Fubara
(74) *Attorney, Agent, or Firm* — WOMBLE BOND DICKINSON (US) LLP

(57) ABSTRACT

Products configured for oral use and methods for preparing such products are provided. In some embodiments, oral products described herein may comprise at least one active ingredient in an amount of 10 weight percent or less, a sugar alcohol, and a gum, such that the product is in the form of a pastille. In some embodiments, oral products described herein may include at least one active ingredient in an amount of about 10 weight percent or less, a sugar substitute, and a sugar alcohol syrup, such that the product is in the form of a lozenge.

56 Claims, No Drawings

(56) References Cited

U.S. PATENT DOCUMENTS

| | | |
|---|---|---|
| 7,900,637 B2 | 3/2011 | Fagerstrom et al. |
| 7,950,399 B2 | 5/2011 | Winterson et al. |
| 8,069,861 B2 | 12/2011 | Sinclair |
| 8,124,147 B2 | 2/2012 | Cheng et al. |
| 8,293,295 B2 | 10/2012 | Andersen et al. |
| 8,336,557 B2 | 12/2012 | Kumar et al. |
| 8,343,532 B2 | 1/2013 | Dam et al. |
| 8,424,541 B2 | 4/2013 | Crawford et al. |
| 8,469,036 B2 | 6/2013 | Williams et al. |
| 8,469,037 B2 | 6/2013 | Liu et al. |
| 8,529,875 B2 | 9/2013 | Andersen |
| 8,529,914 B2 | 9/2013 | Fuisz et al. |
| 8,545,870 B2 | 10/2013 | Dupinay et al. |
| 8,591,967 B2 | 11/2013 | Andersen et al. |
| 8,613,285 B2 | 12/2013 | Fuisz |
| 8,627,828 B2 | 1/2014 | Strickland et al. |
| 8,642,016 B2 | 2/2014 | Chau et al. |
| 8,714,163 B2 | 5/2014 | Kumar et al. |
| 8,741,348 B2 | 6/2014 | Hansson et al. |
| 8,747,562 B2 | 6/2014 | Mishra et al. |
| 8,828,361 B2 | 9/2014 | Anderson |
| 8,833,378 B2 | 9/2014 | Axelsson et al. |
| 8,846,075 B2 | 9/2014 | Johnson et al. |
| 8,858,984 B2 | 10/2014 | Dam et al. |
| 8,863,755 B2 | 10/2014 | Zhuang et al. |
| 8,871,243 B2 | 10/2014 | Fankhauser et al. |
| 8,931,493 B2 | 1/2015 | Sebastian et al. |
| 8,945,593 B2 | 2/2015 | LoCoco et al. |
| 8,978,661 B2 | 3/2015 | Atchley et al. |
| 8,992,974 B2 | 3/2015 | McCarty |
| 9,027,567 B2 | 5/2015 | Gee et al. |
| 9,039,839 B2 | 5/2015 | Beeson et al. |
| 9,044,035 B2 | 6/2015 | Jackson et al. |
| 9,084,439 B2 | 7/2015 | Holton, Jr. |
| 9,155,321 B2 | 10/2015 | Cantrell et al. |
| 9,161,567 B2 | 10/2015 | Shikata et al. |
| 9,161,908 B2 | 10/2015 | Nilsson |
| 9,167,835 B2 | 10/2015 | Sengupta et al. |
| 9,185,931 B2 | 11/2015 | Gao et al. |
| 9,204,667 B2 | 12/2015 | Cantrell et al. |
| 9,237,768 B2 | 1/2016 | Carroll et al. |
| 9,358,296 B2 | 6/2016 | McCarty |
| 9,372,033 B2 | 6/2016 | Lampe et al. |
| 9,386,800 B2 | 7/2016 | Sebastian et al. |
| 9,402,414 B2 | 8/2016 | Griscik et al. |
| 9,402,809 B2 | 8/2016 | Axelsson et al. |
| 9,414,624 B2 | 8/2016 | Carroll et al. |
| 9,420,825 B2 | 8/2016 | Beeson et al. |
| 9,468,233 B2 | 10/2016 | Macko et al. |
| 9,474,303 B2 | 10/2016 | Holton, Jr. |
| 9,521,864 B2 | 12/2016 | Gao et al. |
| 9,565,867 B2 | 2/2017 | Wittorff et al. |
| 9,629,392 B2 | 4/2017 | Holton, Jr. |
| 9,675,102 B2 | 6/2017 | Hunt et al. |
| 9,763,928 B2 | 9/2017 | Duggins et al. |
| 9,775,376 B2 | 10/2017 | Cantrell et al. |
| 9,801,409 B1 | 10/2017 | Smith |
| 9,848,634 B2 | 12/2017 | Fuisz |
| 9,854,830 B2 | 1/2018 | Gao et al. |
| 9,884,015 B2 | 2/2018 | Gao et al. |
| 9,907,748 B2 | 3/2018 | Borschke et al. |
| 9,925,145 B2 | 3/2018 | Hubinette et al. |
| 9,930,909 B2 | 4/2018 | Gao et al. |
| 9,999,243 B2 | 6/2018 | Gao et al. |
| 10,039,309 B2 | 8/2018 | Carroll et al. |
| 10,045,976 B2 | 8/2018 | Fusco et al. |
| 10,092,715 B2 | 10/2018 | Axelsson et al. |
| 10,130,120 B2 | 11/2018 | Mishra et al. |
| 10,143,230 B2 | 12/2018 | Mishra et al. |
| 10,149,850 B2 | 12/2018 | Mishra et al. |
| 10,172,810 B2 | 1/2019 | McCarty |
| 10,244,786 B2 | 4/2019 | Gao et al. |
| 10,334,873 B2 | 7/2019 | Mishra et al. |
| 10,357,054 B2 | 7/2019 | Marshall et al. |
| 10,375,984 B2 | 8/2019 | Hernandez Garcia et al. |
| 10,426,726 B2 | 10/2019 | Neergaard |
| 10,463,070 B2 | 11/2019 | Carroll et al. |
| 10,532,046 B2 | 1/2020 | Rogers et al. |
| 10,543,205 B2 | 1/2020 | Wittorff et al. |
| 11,883,527 B2* | 1/2024 | Holton, Jr. ............. A24B 15/32 |
| 2004/0118422 A1 | 6/2004 | Lundin et al. |
| 2007/0031539 A1 | 2/2007 | Calton |
| 2008/0081071 A1 | 4/2008 | Sanghvi et al. |
| 2008/0166395 A1 | 7/2008 | Roush |
| 2009/0023819 A1 | 1/2009 | Axelsson |
| 2009/0065013 A1 | 3/2009 | Essen et al. |
| 2009/0253754 A1 | 10/2009 | Selmin et al. |
| 2009/0301504 A1 | 12/2009 | Worthen et al. |
| 2010/0004294 A1 | 1/2010 | Axelsson et al. |
| 2010/0061940 A1 | 3/2010 | Axelsson et al. |
| 2010/0187143 A1 | 7/2010 | Essen et al. |
| 2010/0260690 A1 | 10/2010 | Kristensen et al. |
| 2010/0285200 A1* | 11/2010 | Garonzik ................ C12C 5/02 426/597 |
| 2010/0294292 A1 | 11/2010 | Hodin et al. |
| 2011/0139164 A1 | 6/2011 | Mua et al. |
| 2011/0220130 A1 | 9/2011 | Mua et al. |
| 2011/0268809 A1 | 11/2011 | Brinkley et al. |
| 2012/0031415 A1 | 2/2012 | Essen et al. |
| 2012/0037175 A1 | 2/2012 | Cantrell et al. |
| 2013/0078307 A1 | 3/2013 | Holton, Jr. et al. |
| 2013/0118512 A1 | 5/2013 | Jackson et al. |
| 2013/0152953 A1 | 6/2013 | Mua et al. |
| 2013/0177646 A1 | 7/2013 | Hugerth et al. |
| 2013/0206150 A1 | 8/2013 | Duggins et al. |
| 2013/0251779 A1 | 9/2013 | Svandal et al. |
| 2013/0263870 A1* | 10/2013 | Cantrell ................. A24B 15/14 131/355 |
| 2013/0340773 A1 | 12/2013 | Sebastian et al. |
| 2014/0130813 A1 | 5/2014 | Strehle |
| 2014/0154301 A1 | 6/2014 | Chau et al. |
| 2014/0255452 A1 | 9/2014 | Reddick et al. |
| 2015/0068544 A1 | 3/2015 | Moldoveanu et al. |
| 2015/0068545 A1 | 3/2015 | Moldoveanu et al. |
| 2015/0071972 A1 | 3/2015 | Holton, Jr. et al. |
| 2015/0096573 A1 | 4/2015 | Gao et al. |
| 2015/0096574 A1 | 4/2015 | Gao et al. |
| 2015/0096576 A1 | 4/2015 | Gao et al. |
| 2015/0101627 A1* | 4/2015 | Marshall ................ A24B 15/28 131/352 |
| 2015/0296868 A1 | 10/2015 | Sutton |
| 2016/0000140 A1 | 1/2016 | Sebastian et al. |
| 2016/0073676 A1 | 3/2016 | Cantrell et al. |
| 2016/0073689 A1 | 3/2016 | Sebastian et al. |
| 2016/0157515 A1 | 6/2016 | Chapman et al. |
| 2016/0192703 A1 | 7/2016 | Sebastian et al. |
| 2016/0303042 A1 | 10/2016 | Yoshimura et al. |
| 2017/0007594 A1 | 1/2017 | Borschke |
| 2017/0164651 A1 | 6/2017 | Mua et al. |
| 2017/0165252 A1 | 6/2017 | Mua et al. |
| 2017/0172995 A1 | 6/2017 | Repaka et al. |
| 2017/0280764 A1 | 10/2017 | Sahlen et al. |
| 2017/0312261 A1 | 11/2017 | Changoer et al. |
| 2017/0318858 A1* | 11/2017 | Hodin ................. A24F 23/02 |
| 2018/0140007 A1 | 5/2018 | Aspgren et al. |
| 2018/0140521 A1 | 5/2018 | Geonnotti et al. |
| 2018/0140554 A1 | 5/2018 | Wittorff |
| 2018/0153211 A1 | 6/2018 | Persson |
| 2018/0235273 A1 | 8/2018 | Carroll et al. |
| 2018/0255826 A1 | 9/2018 | Persson et al. |
| 2018/0257801 A1 | 9/2018 | Persson |
| 2019/0037909 A1 | 2/2019 | Greenbaum et al. |
| 2019/0255035 A1 | 8/2019 | Bruun |
| 2020/0037638 A1 | 2/2020 | Faraci et al. |
| 2020/0128870 A1 | 4/2020 | Hassler et al. |
| 2020/0138706 A1 | 5/2020 | Rudraraju et al. |
| 2020/0275689 A1 | 9/2020 | Lewerenz |
| 2020/0297026 A1 | 9/2020 | Kannisto et al. |
| 2020/0305496 A1 | 10/2020 | Gessesse |

FOREIGN PATENT DOCUMENTS

| | | |
|---|---|---|
| CN | 103494324 | 1/2014 |
| CN | 105192876 | 12/2015 |

(56) References Cited

FOREIGN PATENT DOCUMENTS

| | | |
|---|---|---|
| CN | 105595404 | 5/2016 |
| CN | 105918603 A | 9/2016 |
| RU | 2250043 C9 | 4/2005 |
| RU | 2302232 C2 | 7/2007 |
| RU | 2313223 C2 | 12/2007 |
| RU | 2339360 C1 | 11/2008 |
| WO | 2018129097 A1 | 7/2018 |
| WO | WO2019/036243 | 2/2019 |

OTHER PUBLICATIONS

Barnscheid et al. (CN 107308124 A), English Translation PE2E, 2017, 50 Pages.

\* cited by examiner

ORAL COMPOSITIONS AND METHODS OF MANUFACTURE

CROSS-REFERENCE TO RELATED APPLICATIONS

The present application is a continuation of International Application No. PCT/IB2020/061473, filed Dec. 4, 2020, which claims priority to and the benefit of U.S. Provisional App. No. 63/036,127, filed Jun. 8, 2020, and a continuation-in-part of U.S. application Ser. No. 16/707,343, filed Dec. 9, 2019, each of which are incorporated herein by reference in their entirety.

FIELD OF THE DISCLOSURE

The present disclosure relates to flavored products intended for human use. The products are configured for oral use and deliver substances such as flavors and/or active ingredients during use. Such products may include tobacco or a product derived from tobacco, or may be tobacco-free alternatives.

BACKGROUND

Tobacco may be enjoyed in a so-called "smokeless" form. Particularly popular smokeless tobacco products are employed by inserting some form of processed tobacco or tobacco-containing formulation into the mouth of the user. Conventional formats for such smokeless tobacco products include moist snuff, snus, and chewing tobacco, which are typically formed almost entirely of particulate, granular, or shredded tobacco, and which are either portioned by the user or presented to the user in individual portions, such as in single-use pouches or sachets. Other traditional forms of smokeless products include compressed or agglomerated forms, such as plugs, tablets, or pellets. Alternative product formats, such as tobacco-containing gums and mixtures of tobacco with other plant materials, are also known. See for example, the types of smokeless tobacco formulations, ingredients, and processing methodologies set forth in U.S. Pat. No. 1,376,586 to Schwartz; U.S. Pat. No. 4,513,756 to Pittman et al.; U.S. Pat. No. 4,528,993 to Sensabaugh, Jr. et al.; U.S. Pat. No. 4,624,269 to Story et al.; U.S. Pat. No. 4,991,599 to Tibbetts; U.S. Pat. No. 4,987,907 to Townsend; U.S. Pat. No. 5,092,352 to Sprinkle, III et al.; U.S. Pat. No. 5,387,416 to White et al.; U.S. Pat. No. 6,668,839 to Williams; U.S. Pat. No. 6,834,654 to Williams; U.S. Pat. No. 6,953,040 to Atchley et al.; U.S. Pat. No. 7,032,601 to Atchley et al.; and U.S. Pat. No. 7,694,686 to Atchley et al.; US Pat. Pub. Nos. 2004/0020503 to Williams; 2005/0115580 to Quinter et al.; 2006/0191548 to Strickland et al.; 2007/0062549 to Holton, Jr. et al.; 2007/0186941 to Holton, Jr. et al.; 2007/0186942 to Strickland et al.; 2008/0029110 to Dube et al.; 2008/0029116 to Robinson et al.; 2008/0173317 to Robinson et al.; 2008/0209586 to Neilsen et al.; 2009/0065013 to Essen et al.; and 2010/0282267 to Atchley, as well as WO2004/095959 to Arnarp et al., each of which is incorporated herein by reference.

Smokeless tobacco product configurations that combine tobacco material with various binders and fillers have been proposed more recently, with example product formats including lozenges, pastilles, gels, extruded forms, and the like. See, for example, the types of products described in US Patent App. Pub. Nos. 2008/0196730 to Engstrom et al.; 2008/0305216 to Crawford et al.; 2009/0293889 to Kumar et al.; 2010/0291245 to Gao et al; 2011/0139164 to Mua et al.; 2012/0037175 to Cantrell et al.; 2012/0055494 to Hunt et al.; 2012/0138073 to Cantrell et al.; 2012/0138074 to Cantrell et al.; 2013/0074855 to Holton, Jr.; 2013/0074856 to Holton, Jr.; 2013/0152953 to Mua et al.; 2013/0274296 to Jackson et al.; 2015/0068545 to Moldoveanu et al.; 2015/0101627 to Marshall et al.; and 2015/0230515 to Lampe et al., each of which is incorporated herein by reference.

All-white snus portions are growing in popularity, and offer a discrete and aesthetically pleasing alternative to traditional snus. Such modern "white" pouched products may include a bleached tobacco or may be tobacco-free.

BRIEF SUMMARY

The present disclosure generally provides oral products and processes for preparing such oral products. The products are intended to impart a taste when used orally, and typically also deliver active ingredients to the consumer, such as nicotine. Such products may also impart desirable organoleptic properties when inserted into the oral cavity of a user of these products.

Accordingly, in one aspect, the disclosure provides oral products including at least one active ingredient in an amount of about 10 percent or less by weight, at least one sugar alcohol in an amount from about 25% to about 45% by weight, and a gum in an amount from about 35% to about 55% by weight, based on the total weight of the product, the product being in the form of a pastille. In some embodiments, the at least one active ingredient may be selected from the group consisting of a nicotine component, botanicals, nutraceuticals, stimulants, amino acids, vitamins, cannabinoids, cannabimimetics, terpenes, and combinations thereof. In certain embodiments, the at least one active ingredient may be selected from the group consisting of caffeine, taurine, GABA, theanine, tryptophan, vitamin B6, vitamin B12 (or other B vitamins), vitamin C, lemon balm extract, ginseng, citicoline, sunflower lecithin, and combinations thereof.

In certain other embodiments, the at least one active ingredient may include a combination of caffeine, taurine, and ascorbic acid. In such embodiments of oral products, for example, the caffeine may be present in an amount of about 2% to about 4% by weight, the taurine may be present in an amount of about 2% to about 4% by weight, and the ascorbic acid may be present in an amount of about 1% to about 3% by weight, based on the total weight of the product. In some embodiments of oral products, the at least one active ingredient may include theanine, gamma-aminobutyric acid, and lemon balm. In such embodiments, for example, the theanine may be present in an amount of about 2% to about 4% by weight, the gamma-aminobutyric acid may be present in an amount of about 2% to about 4% by weight, and the lemon balm may be present in an amount of about 1% to about 3% by weight, based on the total weight of the product. In still other embodiments of oral products, the at least one active ingredient may include caffeine, theanine, and ginseng. In such embodiments, for example, the caffeine may be present in an amount of about 2% to about 4%, the theanine may be present in an amount of about 2% to about 4%, and the ginseng may be present in an amount of about 0.1% to about 1% by weight, based on the total weight of the product.

In some aspects of the disclosure, oral products may include at least one active ingredient, including combinations of active ingredients, being present in an amount in the range of about 6% to about 8% by weight based on the total weight of the product. In some embodiments, oral products as described herein may be substantially free of a tobacco material. In some embodiments, oral products as described herein may be substantially free of nicotine or a nicotine-derived component.

In some embodiments of oral products, the at least one sugar alcohol may be selected from the group consisting of erythritol, arabitol, ribitol, isomalt, maltitol, dulcitol, iditol, mannitol, xylitol, lactitol, sorbitol, and combinations thereof In certain embodiments, the least one sugar alcohol may be selected from the group consisting of isomalt, maltitol, erythritol, and combinations thereof. In such embodiments, for example, the at least one sugar alcohol may include isomalt in an amount from about 20% to about 35% by weight, maltitol in an amount from about 1% to about 10% by weight, and erythritol in an amount from about 0.1% to about 2% by weight, based on the total weight of the product.

In some embodiments, the gum may be selected from the group consisting of gum arabic, xanthan gum, guar gum, ghatti gum, gum tragacanth, karaya gum, locust bean gum, gellan gum, and combinations thereof. In some embodiments, oral products as described herein may include an additive, or combinations of additives, selected from the group consisting of flavorants, sweeteners, additional binders, emulsifiers, disintegration aids, humectants, salts, and mixtures thereof. In some embodiments, the oral product may have an outer coating coated thereon. In some embodiments, the water content of the oral product may be in the range of about 5% to about 20% by weight based on the total weight of the oral product. In certain embodiments, the water content of the oral product may be in the range of about 5% to about 10% by weight based on the total weight of the oral product.

In one or more aspects, the disclosure may provide oral products having various ingredients included therein. For example, in some embodiments, an oral product may include (i) a sugar alcohol in an amount in the range of 25% to 45% by weight, based on the total weight of the composition; (ii) a gum in an amount in the range of about 35% to about 55% by weight; (iii) at least one active ingredient in an amount of about 10% or less by weight; (iv) a humectant in an amount in the range of about 0.1% to about 5% by weight; (v) a salt in an amount in the range of about 0.1% to about 5% by weight; (vi) a flavoring agent in an amount in the range of about 0.1% to about 5% by weight; (vii) a water content in the range of about 5% to about 10% by weight; and (viii) at least about 0.01% by weight of a sweetener.

Some aspects of the present disclosure relate to methods of manufacturing oral products, for example, such as product in the form of a pastille and/or a lozenge. In some embodiments, for example, methods of manufacturing pastille products may include mixing a gum and at least one active ingredient to provide a combined mixture thereof; adding water, at least one additive, and at least one flavoring agent to the combined mixture to provide and aqueous mixture; separately adding at least one sugar alcohol to the aqueous mixture to provide an oral composition; heating the oral composition; depositing the oral composition into a mold; and curing the oral composition to provide an oral product in the form of a pastille. In some embodiments, such methods may include heating the heated gum to a temperature in the range of about 40° C. to about 80° C. In some embodiments, the at least one sugar alcohol may be heated to a temperature in the range of about 160° C. to about 190° C. and then cooled to a temperature in the range of about 120° C. to about 150° C. prior to being added to the aqueous mixture. In some embodiments, the oral composition is heated in the heating step to a temperature in the range of about 60° C. to about 80° C.

Some aspects of the disclosure relate to oral products having at least one active ingredient in an amount of about 10 percent or less by weight based on the total weight of the product, a sugar alcohol, and a gum, the product being in the form of a pastille. In some embodiments, the active ingredient may be present in an amount of about 1 weight percent or less. In some embodiments, the sugar alcohol may comprise sorbitol. In some embodiments, the sugar alcohol may be selected from the group consisting of erythritol, arabitol, ribitol, isomalt, maltitol, dulcitol, iditol, mannitol, xylitol, lactitol, sorbitol, and combinations thereof In some embodiments, the gum may be gum arabic. In some embodiments, the gum may be selected from the group consisting of gum arabic, xanthan gum, guar gum, ghatti gum, gum tragacanth, karaya gum, locust bean gum, gellan gum, and combinations thereof.

In some embodiments, the at least one active ingredient may be selected from the group consisting of a nicotine component, botanicals, nutraceuticals, stimulants, amino acids, vitamins, cannabinoids, cannabimimetics, terpenes, and combinations thereof. In some embodiments, the oral product may include a tobacco material. In certain other embodiments, the oral product may be substantially free of a tobacco material. In some embodiments, oral products of the present disclosure may include an additive selected from the group consisting of flavorants, sweeteners, additional binders, emulsifiers, disintegration aids, humectants, salts, and mixtures thereof.

In some embodiments, the oral product may have an outer coating coated thereon. In some embodiments, the oral product may include a buffering agent and/or a pH adjuster in an amount sufficient to adjust the pH of the oral product to be in the range of about 5.0 to about 7.0. In some embodiments, the buffering agent and/or the pH adjuster may be citric acid, for example. In some embodiments, the water content of the oral product may be in the range of about 5 weight percent to about 20 weight percent based on the total weight of the oral product. In some embodiments, the oral product may include at least about 30 weight percent of at least one sugar alcohol, at least about 40 weight percent of a at least one gum, at least about 2 weight percent of at least one humectant, at least about 0.05 weight percent of at least one sweetener, and at least about 0.1 weight percent of at least one flavoring agent, based on the total weight of the composition.

In some aspects, the disclosure provides oral products that may be in the form of a lozenge. For example, in some embodiments, the disclosure provides oral products including at least one active ingredient in an amount of 10 weight percent or less, a sugar substitute in an amount of at least about 80 weight percent; and a sugar alcohol syrup, the oral product being in the form of a lozenge. In some embodiments, the active ingredient may be present in an amount of 1 weight percent or less. In some embodiments, the sugar substitute may be a non-hygroscopic sugar alcohol capable of forming a glassy matrix. In some embodiments, the sugar substitute may be isomalt, for example. In some embodiments, the sugar substitute may be present in an amount of at least about 85 weight percent. In some embodiments, the sugar substitute may be present in an amount of at least about 90 weight percent. In some embodiments, the sugar substitute may be present in an amount of at least about 95 weight percent. In some embodiments, the sugar alcohol syrup is maltitol syrup.

In some embodiments, oral products according to the present disclosure may include an additive selected from the group consisting of flavorants, sweeteners, additional filler components, emulsifiers, disintegration aids, humectants, salts, and mixtures thereof. In some embodiments, oral products as described herein may include a buffering agent and/or a pH adjuster in an amount sufficient to adjust the pH of the oral product to be in the range of about 5.0 to about 7.0. In some embodiments, the buffering agent and/or the pH adjuster may be citric acid, for example. In some embodiments, the water content of the oral lozenge product may be in the range of about 0.1 weight percent to about 5 weight percent based on the total weight of the oral product.

In some embodiments, the active ingredient may be selected from the group consisting of a nicotine component, botanicals, nutraceuticals, stimulants, amino acids, vitamins, cannabinoids, cannabimimetics, terpenes, and combinations thereof. In some embodiments, the oral product may include a tobacco material. In some embodiments, the tobacco material is in the form of an ultrafiltered tobacco extract. In certain other embodiments, the oral product may be substantially free of a tobacco material. In some embodiments, oral products of the present disclosure may include at least one active ingredient in an amount of 2 weight percent or less, a sugar substitute in an amount of at least about 80 weight percent, at least about 2 weight percent of at least one humectant, at least about 0.1 weight percent of the sugar alcohol syrup, at least about 0.1 weight percent of at least one flavoring agent, and at least about 0.05 weight percent of at least one sweetener, based on the total weight of the composition.

The disclosure includes, without limitations, the following embodiments.

Embodiment 1: An oral product, the oral product comprising at least one active ingredient in an amount of about 10 percent or less by weight based on the total weight of the product, a sugar alcohol, and a gum, the product being in the form of a pastille.

Embodiment 2: The oral product of embodiment 1, wherein the at least one active ingredient is selected from the group consisting of a nicotine component, botanicals, nutraceuticals, stimulants, amino acids, vitamins, cannabinoids, cannabimimetics, terpenes, and combinations thereof.

Embodiment 3: The oral product of any of embodiments 1 to 2, wherein the active ingredient comprises a nicotine component in an amount of about 1 weight percent or less.

Embodiment 4: The oral product of any of embodiments 1 to 3, further comprising a tobacco material.

Embodiment 5: The oral product of any of embodiments 1 to 3, wherein the oral product is substantially free of a tobacco material.

Embodiment 6: The oral product of any of embodiments 1 to 5, wherein the sugar alcohol is selected from the group consisting of erythritol, arabitol, ribitol, isomalt, maltitol, dulcitol, iditol, mannitol, xylitol, lactitol, sorbitol, and combinations thereof.

Embodiment 7: The oral product of any of embodiments 1 to 6, wherein the sugar alcohol comprises sorbitol.

Embodiment 8: The oral product of any of embodiments 1 to 7, wherein the gum is selected from the group consisting of gum arabic, xanthan gum, guar gum, ghatti gum, gum tragacanth, karaya gum, locust bean gum, gellan gum, and combinations thereof.

Embodiment 9: The oral product of any of embodiments 1 to 8, wherein the gum is gum arabic.

Embodiment 10: The oral product of any of embodiments 1 to 9, further comprising an additive selected from the group consisting of flavorants, sweeteners, additional binders, emulsifiers, disintegration aids, humectants, salts, and mixtures thereof.

Embodiment 11: The oral product of any of embodiments 1 to 10, wherein the oral pastille product has an outer coating coated thereon.

Embodiment 12: The oral product of any of embodiments 1 to 11, further comprising a buffering agent and/or a pH adjuster in an amount sufficient to adjust the pH of the oral product to be in the range of about 5.0 to about 7.0.

Embodiment 13: The oral product of any of embodiments 1 to 12, wherein the buffering agent and/or the pH adjuster is citric acid.

Embodiment 14: The oral product of any of embodiments 1 to 13, wherein the water content of the oral product is in the range of about 5 weight percent to about 20 weight percent based on the total weight of the oral product.

Embodiment 15: The oral product of any of embodiments 1 to 14, comprising: at least about 30 weight percent of sugar alcohol, based on the total weight of the composition; at least about 40 weight percent of a at least one gum; at least about 2 weight percent of at least one humectant; at least about 0.05 weight percent of at least one sweetener; and at least about 0.1 weight percent of at least one flavoring agent.

Embodiment 16: An oral product configured for oral use, the oral product comprising at least one active ingredient in an amount of 10 weight percent or less, a sugar substitute in an amount of at least about 80 weight percent; and a sugar alcohol syrup, the oral product being in the form of a lozenge.

Embodiment 17: The oral product of embodiment 16, wherein the at least one active ingredient is selected from the group consisting of a nicotine component, botanicals, nutraceuticals, stimulants, amino acids, vitamins, cannabinoids, cannabimimetics, terpenes, and combinations thereof.

Embodiment 18: The oral product of any of embodiments 16 to 17, wherein the at least one active ingredient comprises a nicotine component in an amount of about 1 weight percent or less.

Embodiment 19: The oral product of any of embodiments 16 to 18, further comprising a tobacco material.

Embodiment 20: The oral product of any of embodiments 16 to 19, wherein the tobacco material is in the form of an ultrafiltered tobacco extract.

Embodiment 21: The oral product of any of embodiments 16 to 18, wherein the oral product is substantially free of a tobacco material.

Embodiment 22: The oral product of any of embodiments 16 to 21, wherein the sugar substitute is a non-hygroscopic sugar alcohol capable of forming a glassy matrix.

Embodiment 23: The oral product of any of embodiments 16 to 22, wherein the sugar substitute is isomalt.

Embodiment 24: The oral product of any of embodiments 16 to 23, wherein the sugar substitute is present in an amount of at least about 85 weight percent.

Embodiment 25: The oral product of any of embodiments 16 to 24, wherein the sugar substitute is present in an amount of at least about 90 weight percent.

Embodiment 26: The oral product of any of embodiments 16 to 25, wherein the sugar substitute is present in an amount of at least about 95 weight percent.

Embodiment 27: The oral product of any of embodiments 16 to 26, wherein the sugar alcohol syrup is maltitol syrup.

Embodiment 28: The oral product of any of embodiments 16 to 27, further comprising an additive selected from the group consisting of flavorants, sweeteners, additional filler components, emulsifiers, disintegration aids, humectants, salts, and mixtures thereof.

Embodiment 29: The oral product of any of embodiments 16 to 28, further comprising a buffering agent and/or a pH adjuster in an amount sufficient to adjust the pH of the oral product to be in the range of about 5.0 to about 7.0.

Embodiment 30: The oral product of any of embodiments 16 to 29, wherein the buffering agent and/or the pH adjuster is citric acid.

Embodiment 31: The oral product of any of embodiments 16 to 30, wherein the water content of the oral product is in the range of about 0.1 weight percent to about 5 weight percent based on the total weight of the oral product.

Embodiment 32: The oral product of any of embodiments 16 to 31, comprising at least about 80 weight percent of the sugar substitute; at least about 2 weight percent of at least one humectant; at least about 0.1 weight percent of the sugar alcohol syrup; at least about 0.1 weight percent of at least one flavoring agent; and at least about 0.05 weight percent of at least one sweetener.

Embodiment 33: Use of at least one active ingredient in an oral product, wherein the active ingredient is present in an amount of 10 percent or less by weight based on the total weight of the product.

Embodiment 34: Use of at least one active ingredient in the oral product of embodiment 33, wherein the oral product is substantially free of a tobacco material.

Embodiment 35: Use of at least one active ingredient in the oral product of any of embodiments 33 to 34, wherein the oral product is in the form of a pastille or in the form of a lozenge.

Embodiment 36: Use of a nicotine component in an oral product, wherein the nicotine component is present in an amount of 1 percent or less by weight based on the total weight of the product.

Embodiment 37: Use of a nicotine component in the oral product of embodiment 36, wherein the oral product is substantially free of a tobacco material.

Embodiment 38: Use of a nicotine component in the oral product of any of embodiments 36 to 37, wherein the oral product is in the form of a pastille or in the form of a lozenge.

Embodiment 39: An oral product, the oral product comprising at least one active ingredient in an amount of about 10 percent or less by weight, at least one sugar alcohol in an amount from about 25% to about 45% by weight, and a gum in an amount from about 35% to about 55% by weight, based on the total weight of the product, the product being in the form of a pastille.

Embodiment 40: The oral product of embodiment 39, wherein the at least one active ingredient is selected from the group consisting of a nicotine component, botanicals, nutraceuticals, stimulants, amino acids, vitamins, cannabinoids, cannabimimetics, terpenes, and combinations thereof.

Embodiment 41: The oral product of any of embodiments 39-40, wherein the at least one active ingredient is selected from the group consisting of caffeine, taurine, GABA, theanine, tryptophan, vitamin B6, vitamin B12, vitamin C, lemon balm extract, ginseng, citicoline, sunflower lecithin, and combinations thereof.

Embodiment 42: The oral product of any of embodiments 39-41, wherein the at least one active ingredient comprises a combination of caffeine, taurine, and ascorbic acid, optionally further comprising trisodium citrate.

Embodiment 43: The oral product of embodiment 42, wherein the caffeine is present in an amount of about 2% to about 4% by weight, the taurine is present in an amount of about 2% to about 4% by weight, and the ascorbic acid is present in an amount of about 1% to about 3% by weight, based on the total weight of the product.

Embodiment 44: The oral product of any of embodiments 39-41, wherein the at least one active ingredient comprises theanine, gamma-aminobutyric acid, and optionally lemon balm.

Embodiment 45: The oral product of embodiment 44, wherein the theanine is present in an amount of about 2% to about 4% by weight, the gamma-aminobutyric acid is present in an amount of about 2% to about 4% by weight, and the lemon balm is present in an amount of about 1% to about 3% by weight, based on the total weight of the product.

Embodiment 46: The oral product of any of embodiments 39-41, wherein the at least one active ingredient comprises caffeine, theanine, and optionally ginseng.

Embodiment 47: The oral product of embodiment 46, wherein the caffeine is present in an amount of about 2% to about 4%, the theanine is present in an amount of about 2% to about 4%, and the ginseng is present in an amount of about 0.1% to about 1% by weight, based on the total weight of the product.

Embodiment 48: The oral product of any of embodiments 39-47, wherein the at least one active ingredient is present in an amount in the range of about 6% to about 8% by weight based on the total weight of the product.

Embodiment 49: The oral product of any of embodiments 39-48, wherein the oral product is substantially free of a tobacco material.

Embodiment 50: The oral product of any of embodiments 39-49, wherein the oral product is substantially free of nicotine or a nicotine-derived component.

Embodiment 51: The oral product of any of embodiments 39-50, wherein the at least one sugar alcohol is selected from the group consisting of erythritol, arabitol, ribitol, isomalt, maltitol, dulcitol, iditol, mannitol, xylitol, lactitol, sorbitol, and combinations thereof.

Embodiment 52: The oral product any of embodiments 39-51, wherein the least one sugar alcohol is selected from the group consisting of isomalt, maltitol, erythritol, and combinations thereof.

Embodiment 53: The oral product of any of embodiments 39-52, wherein the at least one sugar alcohol comprises isomalt in an amount from about 20% to about 35% by weight, maltitol in an amount from about 1% to about 10% by weight, and erythritol in an amount from about 0.1% to about 2% by weight, based on the total weight of the product.

Embodiment 54: The oral product of any of embodiments 39-53, wherein the gum is selected from the group consisting of gum arabic, xanthan gum, guar gum, ghatti gum, gum tragacanth, karaya gum, locust bean gum, gellan gum, and combinations thereof.

Embodiment 55: The oral product of any of embodiments 39-54, further comprising an additive selected from the group consisting of flavorants, sweeteners, additional binders, emulsifiers, disintegration aids, humectants, salts, and mixtures thereof.

Embodiment 56: The oral product of any of embodiments 39-55, wherein the oral pastille product has an outer coating coated thereon.

Embodiment 57: The oral product of any of embodiments 39-56, wherein the water content of the oral product is in the range of about 5% to about 20% by weight based on the total weight of the oral product.

Embodiment 58: The oral product of any of embodiments 39-57, wherein the water content of the oral product is in the range of about 5% to about 10% by weight based on the total weight of the oral product.

Embodiment 59: An oral product, comprising: a sugar alcohol in an amount in the range of 25% to 45% by weight, based on the total weight of the composition; a gum in an amount in the range of about 35% to about 55% by weight; at least one active ingredient in an amount of about 10% or less by weight; a humectant in an amount in the range of about 0.1% to about 5% by weight; a salt in an amount in the range of about 0.1% to about 5% by weight; a flavoring agent in an amount in the range of about 0.1% to about 5% by weight; a water content in the range of about 5% to about 10% by weight; and at least about 0.01% by weight of a sweetener.

Embodiment 60: A method of preparing an oral product, the method comprising: mixing a gum and at least one active ingredient to provide a combined mixture thereof; adding water, at least one additive, and at least one flavoring agent to the combined mixture to provide an aqueous mixture; separately adding at least one sugar alcohol to the aqueous mixture to provide an oral composition; heating the oral composition; depositing the oral composition into a mold; and curing the oral composition to provide an oral product in the form of a pastille.

Embodiment 61: The method of embodiment 60, wherein the gum is heated to a temperature in the range of about 40° C. to about 80° C.

Embodiment 62: The method to any of embodiments 60-61, wherein the at least one sugar alcohol is heated to a temperature in the range of about 160° C. to about 190° C. and then optionally cooled to a temperature in the range of about 120° C. to about 150° C. prior to being added to the aqueous mixture.

Embodiment 63: The method of any of embodiments 60-62, wherein heating the oral composition comprises heating to a temperature in the range of about 60° C. to about 80° C.

Embodiment 64: The method of any of embodiments 60-63, wherein the at least on active ingredient is selected from the group consisting of a nicotine component, botanicals, nutraceuticals, stimulants, amino acids, vitamins, cannabinoids, cannabimimetics, terpenes, and combinations thereof.

Embodiment 65: The method of any of embodiments 60-64, wherein the at least one sugar alcohol is selected from the group consisting of erythritol, arabitol, ribitol, isomalt, maltitol, dulcitol, iditol, mannitol, xylitol, lactitol, sorbitol, and combinations thereof.

Embodiment 66: The method of any of embodiments 60-65, wherein the at least one additive selected from the group consisting of flavorants, sweeteners, additional binders, emulsifiers, disintegration aids, humectants, salts, and mixtures thereof.

Embodiment 67: An oral product, the oral product comprising an active ingredient in an amount of 10 weight percent or less, a sugar substitute in an amount of at least about 80 weight percent; and a sugar alcohol syrup, the oral product being in the form of a lozenge.

Embodiment 68: The oral product of embodiment 67, wherein the at least one active ingredient is selected from the group consisting of a nicotine component, botanicals, nutraceuticals, stimulants, amino acids, vitamins, cannabinoids, cannabimimetics, terpenes, and combinations thereof.

Embodiment 69: The oral product of any one of embodiments 67-68, wherein the at least one active ingredient is selected from the group consisting of caffeine, taurine, GABA, theanine, tryptophan, vitamin B6, vitamin B12, vitamin C, lemon balm extract, ginseng, citicoline, sunflower lecithin, and combinations thereof.

Embodiment 70: The oral product of any one of embodiments 67-69, wherein the at least one active ingredient comprises a combination of caffeine, taurine, and ascorbic acid.

Embodiment 71: The oral product of embodiment 70, wherein the caffeine is present in an amount of about 2% to about 4% by weight, the taurine is present in an amount of about 2% to about 4% by weight, and the ascorbic acid is present in an amount of about 1% to about 3% by weight, based on the total weight of the product.

Embodiment 72: The oral product of any one of embodiments 67-69, wherein the at least one active ingredient comprises theanine, gamma-aminobutyric acid, and optionally lemon balm.

Embodiment 73: The oral product of embodiment 72, wherein the theanine is present in an amount of about 2% to about 4% by weight, the gamma-aminobutyric acid is present in an amount of about 2% to about 4% by weight, and the lemon balm is present in an amount of about 1% to about 3% by weight, based on the total weight of the product.

Embodiment 74: The oral product of any one of embodiments 67-69, wherein the at least one active ingredient comprises caffeine, theanine, and optionally ginseng.

Embodiment 75: The oral product of embodiment 74, wherein the caffeine is present in an amount of about 2% to about 4%, the theanine is present in an amount of about 2% to about 4% by weight, and the ginseng is present in an amount of about 0.1% to about 1% by weight, based on the total weight of the product.

Embodiment 76: The oral product of any one of embodiments 67-75, wherein the at least one active ingredient is present in an amount in the range of about 6% to about 8% by weight based on the total weight of the product.

Embodiment 77: The oral product of any one of embodiments 67-76, wherein the oral product is free of a tobacco material.

Embodiment 78: The oral product of any one of embodiments 67-77, wherein the oral product is free of nicotine or a nicotine-derived component.

Embodiment 79: The oral product of any one of embodiments 67-78, further comprising a tobacco material.

Embodiment 80: The oral product of any one of embodiments 67-79, wherein the sugar substitute is a non-hygroscopic sugar alcohol capable of forming a glassy matrix.

Embodiment 81: The oral product of any one of embodiments 67-80, wherein the sugar substitute is isomalt.

Embodiment 82: The oral product of any one of embodiments 67-81, wherein the sugar substitute is present in an amount of at least about 85 weight percent.

Embodiment 83: The oral product of any one of embodiments 67-82, wherein the sugar substitute is present in an amount of at least about 90 weight percent.

Embodiment 84: The oral product of any one of embodiments 67-83, wherein the sugar substitute is present in an amount of at least about 95 weight percent.

Embodiment 85: The oral product of any one of embodiments 67-84, wherein the sugar alcohol syrup is maltitol syrup.

Embodiment 86: The oral product of any one of embodiments 67-85, further comprising an additive selected from the group consisting of flavorants, sweeteners, additional filler components, emulsifiers, disintegration aids, humectants, salts, and mixtures thereof.

Embodiment 87: The oral product of any one of embodiments 67-86, further comprising a buffering agent and/or a pH adjuster in an amount sufficient to adjust the pH of the oral product to be in the range of about 5.0 to about 7.0.

Embodiment 88: The oral product of any one of embodiments 67-87, wherein the water content of the oral product is in the range of about 0.1 weight percent to about 5 weight percent based on the total weight of the oral product.

Embodiment 89: The oral product of any one of embodiments 1-88, wherein the at least one active ingredient comprises:
theanine;
theanine and tryptophan; or
theanine and vitamin B6, vitamin B12, or both.

Embodiment 90: The oral product of embodiment 89, comprising theanine and one or both of vitamins B6 and vitamin B12.

Embodiment 91: The oral product of any one of embodiments 1-90, further comprising magnesium, such as magnesium in an amount by weight from about 0.1% to about 2%, or from about 0.2 to about 1%, based on elemental magnesium.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

DETAILED DESCRIPTION

The present disclosure will now be described more fully hereinafter with reference to example embodiments thereof. These example embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in this specification and the claims, the singular forms "a," "an," and "the" include plural referents unless the context clearly dictates otherwise. Reference to "dry weight percent" or "dry weight basis" refers to weight on the basis of dry ingredients (i.e., all ingredients except water). Reference to "wet weight" refers to the weight of the mixture including water. Unless otherwise indicated, reference to "weight percent" of a mixture reflects the total wet weight of the mixture (i.e., including water).

The disclosure provides products configured for oral use and processes for preparing such oral products. Oral products as described herein may generally include a mixture of ingredients in the form of a composition. For example, in some embodiments, the compositions provided herein may include one or more active ingredients (e.g., a tobacco material and/or nicotine) and one or more additives (e.g., a filler, a binder component, a flavorant, etc..) that combine to form a product configured for oral use.

Oral products as described herein may be provided in various different forms and with various combinations of ingredients. Particularly, in preferred embodiments, products of the present disclosure may be provided in one of two forms, for example, in the form of a pastille-type product or a lozenge-type product. The pastille- and lozenge-type products according to embodiments of the present disclosure may be configured for oral use and advantageously can provide different characteristics and properties upon insertion into the oral cavity of a user of that product. Certain products can exhibit, for example, one or more of the following characteristics: crispy, granular, chewy, syrupy, pasty, fluffy, smooth, and/or creamy. In certain embodiments, the desired textural property can be selected from the group consisting of adhesiveness, cohesiveness, density, dryness, fracturability, graininess, gumminess, hardness, heaviness, moisture absorption, moisture release, mouthcoating, roughness, slipperiness, smoothness, viscosity, wetness, and combinations thereof.

The term "configured for oral use" as used herein means that the product is provided in a form such that during use, saliva in the mouth of the user causes one or more of the components of the product (e.g., flavoring agents and/or nicotine) to pass into the mouth of the user. In one embodiment, the product is adapted to deliver components to a user through mucous membranes in the user's mouth and, in addition, said component is an active ingredient (including, but not limited to, for example, nicotine) that can be absorbed through the mucous membranes in the mouth when the product is used. In some embodiments, the product may be adapted to deliver flavor components to a user in addition to the active ingredient.

The products comprising the compositions of the present disclosure may be dissolvable. As used herein, the terms "dissolve," "dissolving," and "dissolvable" refer to compositions having aqueous-soluble components that interact with moisture in the oral cavity and enter into solution, thereby causing gradual consumption of the product. According to one aspect, the dissolvable product is capable of lasting in the user's mouth for a given period of time until it completely dissolves. Dissolution rates can vary over a wide range, from about 1 minute or less to about 60 minutes. For example, fast release mixtures typically dissolve and/or release the active substance in about 2 minutes or less, often about 1 minute or less (e.g., about 50 seconds or less, about 40 seconds or less, about 30 seconds or less, or about 20 seconds or less). Dissolution can occur by any means, such as melting, mechanical disruption (e.g., chewing), enzymatic or other chemical degradation, or by disruption of the interaction between the components of the mixture. In some embodiments, the product can be meltable as discussed, for example, in US Patent App. Pub. No. 2012/0037175 to Cantrell et al. In other embodiments, the products do not dissolve during the product's residence in the user's mouth.

In some embodiments, the products disclosed herein may be in the form of a dissolvable and lightly chewable pastille product for oral use. As used herein, the term "pastille" refers to a dissolvable oral product made by solidifying a liquid or gel composition, such as a composition that includes a gelling or binding agent, so that the final product is a hardened solid gel. In certain embodiments, the pastille products of the disclosure are characterized by sufficient cohesiveness to withstand light chewing action in the oral cavity without rapidly disintegrating. The pastille products of the disclosure typically do not exhibit a highly deformable chewing quality as found in conventional chewing gum. See, for example, the smokeless tobacco pastilles, pastille formulations, pastille configurations, pastille characteristics and techniques for formulating or manufacturing pastilles set forth in U.S. Pat. No. 9,204,667 to Cantrell et al.; U.S. Pat. No. 9,775,376 to Cantrell et al.; U.S. Pat. No. 10,357,054 to Marshall et al.; which are incorporated herein by reference.

Alternatively, in some embodiments, the products disclosed herein may be in the form of a dissolvable lozenge product configured for oral use. Example lozenge-type products of the invention have the form of a lozenge, tablet, microtab, or other tablet-type product. See, for example, the types of nicotine-containing lozenges, lozenge formulations, lozenge formats and configurations, lozenge characteristics and techniques for formulating or manufacturing lozenges set forth in U.S. Pat. No. 4,967,773 to Shaw; U.S. Pat. No. 5,110,605 to Acharya; U.S. Pat. No. 5,733,574 to Dam; U.S. Pat. No. 6,280,761 to Santus; U.S. Pat. No. 6,676,959 to Andersson et al.; U.S. Pat. No. 6,248,760 to Wilhelmsen; and 7,374,779; US Pat. Pub. Nos. 2001/0016593 to Wilhelmsen; 2004/0101543 to Liu et al.; 2006/0120974 to Mcneight; 2008/0020050 to Chau et al.; 2009/0081291 to Gin et al.; and 2010/0004294 to Axelsson et al.; which are incorporated herein by reference. Such lozenge-type products, in some embodiments, may exhibit translucence or transparency. The desired transparency or translucency of the product can be quantified by any known method. For example, optical methods such as turbidimetry (or nephelometry) and colorimetry may be used to quantify the cloudiness (light scattering) and the color (light absorption), respectively, of the products. Translucency can also be confirmed by visual inspection by simply holding the product up to a light source and determining if light travels through the material or product in a diffuse manner.

Oral products of the present disclosure may be provided in the specific physical forms noted above (e.g., such as in the form of a pastille or a lozenge) by altering the water content, for example, the water content of the products may be provided within a specified range so as to dictate the final form of the product. The water content of the products described herein, prior to use by a consumer of the product, may vary within such ranges according to the desired properties and characteristics, in addition to dictating the final form of the product. For example, pastille-type products typically possess a water content in the range of about 5 to about 20 weight percent, based on the total weight of the composition. Preferably, the moisture content of a pastille product, as present within a single unit of product prior to insertion into the mouth of the user, is within the range of about 5 to about 25 weight percent, often about 8 to about 20 weight percent, more often about 10 to about 15 weight percent, based on the total weight of the product unit. In some embodiments, the moisture content of a pastille product may be at least about 5 weight percent, at least about 10 weight percent, at least about 15 weight percent, or at least about 20 weight percent, based on the total weight of the product.

Alternatively, lozenge-type products typically possess a water content in the range of about 0.1 to about 5 weight percent, based on the total weight of the composition. Preferably, the moisture content of a lozenge product, as present within a single unit of product prior to insertion into the mouth of the user, is less than about 5 weight percent, less than about 3 weight percent, less than about 2 weight percent, or less than about 1 weight percent, based on the total weight of the product unit. In some embodiments, the moisture content of a lozenge product as described herein may be within the range of about 0.1 to about 5 weight percent, about 0.5 to about 3 weight percent, or about 1 to about 2 weight percent, based on the total weight of the product.

As noted above, the pastille- and lozenge-type products of the present disclosure may incorporate various different additives in addition to at least one active ingredient and may be prepared according to a variety of different methods commonly known in the art for preparing pastille- and lozenge-type products. Example compositions, products, and methods of preparing such products will be detailed herein below.

Pastille Products

Pastille products of the present disclosure typically include a composition comprising at least one active ingredient in an amount of less than about 10 weight percent (e.g., a nicotine compound), a gum, and a sugar alcohol as a filler component. Any active ingredient (e.g., a tobacco material and/or an active ingredient) as discussed herein below is meant to be suitable for use as an active ingredient in the pastille compositions according to the present disclosure. Such active ingredients may be added as a singular active ingredient, or in combinations with one or more other active ingredients. In some embodiments, the active ingredient may be provided in liquid form or in a dry powder or particulate form. As noted above, the active ingredient typically is present in an amount from about 0.1 weight percent to about 10 weight percent, such as, e.g., from about 0.1 weight percent, about 0.5 weight percent, about 1 weight percent, about 1.5 weight percent, about 2 weight percent, about 2.5 weight percent, about 3 weight percent, about 3.5 weight percent, about 4 weight percent, or about 4.5 weight percent, to about 5.5 weight percent, about 6 weight percent, about 6.5 weight percent, about 7 weight percent, about 7.5 weight percent, about 8 weight percent, about 8.5 weight percent, about 9 weight percent, about 9.5 weight percent, or about 10 weight percent, based on the total weight of the composition. In some embodiments, the active ingredient may be present in an amount of less than about 10 weight percent, less than about 9 weight percent, less than about 8 weight percent, less than about 7 weight percent, less than about 6 weight percent, less than about 5 weight percent, less than about 4 weight percent, less than about 3 weight percent, less than about 2 weight percent, or less than about 1 weight percent, based on the total weight of the composition.

A gum (or combination of two or more gums) may be employed in amounts sufficient to provide the desired physical attributes and physical integrity to the pastille products. In some embodiments, the gum may function as a binder component in the oral product. A representative amount of gum may make up at least about 5 percent or at least about 10 percent of the total weight of the pastille composition. In certain embodiments, the gum(s) of the composition will be present in an amount of at least about 30 weight percent, at least about 35 weight percent, at least about 40 weight percent, at least about 45 weight percent, or at least about 50 weight percent, based on the total weight of the composition. In some embodiments, the gum in the composition may be present in an amount of about 35 weight percent to about 55 weight percent, based on the total weight of the composition. Preferably, the total amount of gum within the pastille product will not exceed about 55 percent of the total weight of the composition. Often, the amount of gum within a desirable composition will not exceed about 65 percent, and frequently will not exceed about 60 percent, of the total weight of the composition.

In certain embodiments, the gum includes a natural gum. Particularly, natural gums (e.g., such as gum arabic) may be incorporated into the pastille products as a softener. Advantageously, use of a natural gum as a softener provides the desired textural qualities necessary for forming pastille compositions, particularly those described herein. Particularly, it should be noted that increasing the amount of a natural gum (e.g., gum arabic) while, subsequently, decreasing the amount of sugar alcohol can advantageously increase softness in the resulting pastille product. As used herein, a natural gum refers to polysaccharide materials of natural origin that are useful as softening agents. Representative natural gums derived from plants, which are typically water soluble to some degree, include xanthan gum, guar gum, gum arabic, ghatti gum, gum tragacanth, karaya gum, locust bean gum, gellan gum, and combinations thereof. Preferably, gum arabic may be used as an example natural gum which provides the above noted softening characteristics when incorporated into the pastille compositions of the present disclosure.

In some embodiments, the gum can optionally include a tobacco-derived material in the form of a binder, which can be combined with one or more additional binder components. For example, in one particular embodiment, the gum component comprises gum arabic in combination with a tobacco-derived binder as described herein. In such embodiments, the amount of tobacco-derived binder within the composition is at least about 0.5 percent or at least about 1 percent or at least about 1.5 percent, on a weight basis of the composition. An example weight range is about 0.5 to about 10 weight percent, more often about 1 to about 5 weight percent.

As noted above, pastille products of the present disclosure may comprise at least one sugar alcohol in the form of a filler component. Sugar alcohols are particularly advantageous as filler components in the pastilles of the disclosure because such materials contribute some sweetness and do not disrupt the desired chewable characteristics of the final product. Sugar alcohols are polyols derived from monosaccharides or disaccharides that have a partially or fully hydrogenated form. Example sugar alcohols have between about 4 and about 20 carbon atoms and include erythritol, arabitol, ribitol, isomalt, maltitol, dulcitol, iditol, mannitol, xylitol, lactitol, sorbitol, and combinations thereof (e.g., hydrogenated starch hydrolysates). In some embodiments, isomalt may be incorporated as the sole filler component. A sugar alcohol is typically added to compositions of the disclosure in the form of an aqueous solution or suspension, such as a solution or suspension with a solids content of about 50 to about 90 weight percent. Combinations of a sugar alcohol with a further filler component can also be used. A filler component often fulfills multiple functions, such as enhancing certain organoleptic properties such as texture and mouthfeel, enhancing cohesiveness or compressibility of the product, and the like. When present, a representative amount of filler, whether an organic and/or inorganic filler, may make up at least about 10 percent, at least about 20 percent, or at least about 25 percent, based on the total weight of the composition. Preferably, the amount of filler within the composition will not exceed about 50 percent, and frequently will not exceed about 40 percent, of the total weight of the composition. A typical filler range is about 15 weight percent to about 50 weight percent, about 25 weight percent to about 45 weight percent, or about 30 weight percent to about 40 weight percent.

Lozenge Products

Lozenge products of the present disclosure typically include composition comprising at least one active ingredient in an amount of less than about 2 weight percent (e.g., a nicotine compound), a sugar substitute in an amount of at least about 80 weight percent, and a sugar alcohol syrup. Any active ingredient (e.g., a tobacco material and/or an active ingredient) as discussed herein below is meant to be suitable for use as an active ingredient in the lozenge compositions provided herein. Such active ingredients may be added as a singular active ingredient, or in combinations with one or more other active ingredients. In some embodiments, the active ingredient may be provided in liquid form or in a dry powder or particulate form. As noted above, the active ingredient typically is present in an amount from about 0.1 weight percent to about 10 weight percent, such as, e.g., from about 0.1 weight percent to about 10 weight percent, such as, e.g., from about 0.1 weight percent, about 0.5 weight percent, about 1 weight percent, about 1.5 weight percent, about 2 weight percent, about 2.5 weight percent, about 3 weight percent, about 3.5 weight percent, about 4 weight percent, or about 4.5 weight percent, to about 5.5 weight percent, about 6 weight percent, about 6.5 weight percent, about 7 weight percent, about 7.5 weight percent, about 8 weight percent, about 8.5 weight percent, about 9 weight percent, about 9.5 weight percent, or about 10 weight percent, based on the total weight of the composition. In some embodiments, the active ingredient may be present in an amount of less than about 10 weight percent, less than about 9 weight percent, less than about 8 weight percent, less than about 7 weight percent, less than about 6 weight percent, less than about 5 weight percent, less than about 4 weight percent, less than about 3 weight percent, less than about 2 weight percent, or less than about 1 weight percent, based on the total weight of the composition.

In some embodiments, the lozenge product comprises a sugar substitute. The sugar substitute is typically provided in pure, solid form (e.g., granular or powdered form). In certain embodiments, the sugar substitute is dry, comprising a very low water content. For example, the sugar substitute can comprise less than about 5% water by weight, less than about 3% water by weight, less than about 2% water by weight, or less than about 1% water by weight.

The sugar substitute can be any sugarless material (i.e., sucrose-free material) and can be natural or synthetically produced. The sugar substitute used in the products described herein can be nutritive or non-nutritive. For example, the sugar substitute is commonly a sugar alcohol. Sugar alcohols that may be useful according to the present invention include, but are not limited to, erythritol, threitol, arabitol, xylitol, ribotol, mannitol, sorbitol, dulcitol, iditol, isomalt, maltitol, lactitol, polyglycitol, and mixtures thereof. For example, in certain embodiments, the sugar alcohol is selected from the group consisting of erythritol, sorbitol, and isomalt. The amount of sugar substitute in the lozenge compositions can vary, but is typically at least about 75%, at least about 80%, at least about 85%, or at least about 90%, or at least about 95% by weight of the composition.

In certain embodiments, the sugar substitute is capable of forming a glassy matrix. The formation of a glassy matrix is commonly characterized by a translucent/transparent appearance. Typically, the sugar substitute is substantially non-hygroscopic. Non-hygroscopic materials typically do not absorb, adsorb, and/or retain a significant quantity of moisture from the air. For example, in some embodiments, the sugar substitute exhibits a weight gain of water of less than about 50% upon exposure to conditions of 25° C., 80% relative humidity for two weeks. Typically, the sugar substitute exhibits a weight gain of less than about 30%, less than about 20%, less than about 10%, less than about 5%, less than about 2%, or less than about 1% upon exposure to conditions of 25° C., 80% relative humidity for two weeks. Non-hygroscopic materials can provide the benefit of reducing the tendency of the lozenge product to tackify upon exposure to humidity.

In certain embodiments, the sugar substitute comprises one or more sugar alcohols. For example, in one embodiment, the sugar substitute is isomalt. Isomalt is a disaccharide that is typically made by enzymatic rearrangement of sucrose into isomaltulose, followed by hydrogenation to give an equimolar composition of 6-O-α-D-glucopyranosido-D-sorbitol (1,6-GPS) and 1-O-α-D-glucopyranosido-D-mannitol-dihydrate (1,1-GPM-dihydrate).

In some embodiments, the lozenge products of the present disclosure may comprise a syrup, e.g., a sugar syrup or a sugar alcohol syrup. "Sugar alcohol syrup" as used herein is intended to refer to a thick solution of sugar alcohol in water, e.g., having greater than about 40% solids, preferably having greater than about 50% solids, greater than about 60% solids, greater than about 70% solids, or greater than about 80% solids. Typically, the solid content of the sugar alcohol syrup primarily comprises the named sugar alcohol (i.e., maltitol syrup typically comprises greater than about 80%, greater than about 85%, or greater than about 90% by weight maltitol on a dry basis). Sugar alcohol syrups are generally prepared by heating a solution of the sugar alcohol in water and cooling the mixture to give a viscous composition. The resulting syrup is typically characterized by a relatively high concentration of sugar alcohol and relatively high stability (i.e., the sugar alcohol typically does not crystallize from solution, e.g., at room temperature).

The syrup, e.g., sugar alcohol syrup, desirably is capable of affecting the re-crystallization of a melted sugar substitute. One example sugar alcohol syrup that is particularly useful according to the present disclosure is maltitol syrup. Other sugar alcohol syrups can be used, including, but not limited to, corn syrup, golden syrup, molasses, xylitol, mannitol, glycerol, erythritol, threitol, arabitol, ribitol, mannitol, sorbitol, dulcitol, iditol, isomalt, lactitol, and polyglycitol syrups. Such sugar alcohol syrups can be prepared or can be obtained from commercial sources. For example, maltitol syrups are commercially available from such suppliers as Corn Products Specialty Ingredients. Although sugar alcohol syrups may be preferred, sugar syrups can, in certain embodiments, be used in place of or in combination with the sugar alcohol syrup. For example, in some embodiments, corn syrup, golden syrup, and/or molasses can be used.

The amount of sugar alcohol syrup added to the lozenge composition mixture is typically that amount required to slow recrystallization of the sugar substitute in melted form. It should be noted that it may be possible to vary the amount of sugar alcohol syrup depending on the composition of the remaining ingredients to ensure that the recrystallization is sufficiently slow to provide a material with the desired characteristics (e.g., a desired level of translucency/transparency). Accordingly, the amount of sugar alcohol syrup can vary, but typically ranges from about 0.1% to about 2%, often from about 0.5% to about 1.5%, and more often about 1% by weight of the smokeless tobacco product mixture. In certain embodiments, the amount of sugar alcohol syrup is higher, for example, up to about 2% by weight of the mixture, up to about 5% by weight of the mixture, up to about 10% by weight of the mixture, or up to about 20% by weight of the mixture Active Ingredient The compositions and products as disclosed herein includes one or more active ingredients. As used herein, an "active ingredient" refers to one or more substances belonging to any of the following categories: API (active pharmaceutical ingredient), food additives, natural medicaments, and naturally occurring substances that can have an effect on humans. Example active ingredients include any ingredient known to impact one or more biological functions within the body, such as ingredients that furnish pharmacological activity or other direct effect in the diagnosis, cure, mitigation, treatment, or prevention of disease, or which affect the structure or any function of the body of humans (e.g., provide a stimulating action on the central nervous system, have an energizing effect, an antipyretic or analgesic action, or an otherwise useful effect on the body). In some embodiments, the active ingredient may be of the type generally referred to as dietary supplements, nutraceuticals, "phytochemicals" or "functional foods." These types of additives are sometimes defined in the art as encompassing substances typically available from naturally-occurring sources (e.g., botanical materials) that provide one or more advantageous biological effects (e.g., health promotion, disease prevention, or other medicinal properties), but are not classified or regulated as drugs.

Non-limiting examples of active ingredients include those falling in the categories of botanical ingredients, stimulants, amino acids, nicotine components, and/or pharmaceutical, nutraceutical, and medicinal ingredients (e.g., vitamins, such as A, B3, B6, B12, and C, and/or cannabinoids, such as tetrahydrocannabinol (THC) and cannabidiol (CBD)). Each of these categories is further described herein below. The particular choice of active ingredients will vary depending upon the desired flavor, texture, and desired characteristics of the particular product.

In certain embodiments, the active ingredient is selected from the group consisting of caffeine, taurine, GABA, theanine, tryptophan, vitamin B6, vitamin B12, vitamin C, lemon balm extract, ginseng, citicoline, sunflower lecithin, and combinations thereof. For example, the active ingredient can include a combination of caffeine, theanine, and optionally ginseng. In another embodiment, the active ingredient includes a combination of theanine, gamma-amino butyric acid (GABA), and optionally lemon balm extract. In a further embodiment, the active ingredient includes theanine, theanine and tryptophan, theanine and one or more of B vitamin B6 and vitamin B12, or tryptophan, theanine and one or more of B vitamin B6 and vitamin B12. In a still further embodiment, the active ingredient includes a combination of caffeine, taurine, and vitamin C, optionally further including one or more B vitaimins (e.g., vitamin B6 or B12). A magnesium salt (e.g., magnesium gluconate) could be added to any of the above combinations, particularly combinations also including theanine.

The particular percentages of active ingredients present will vary depending upon the desired characteristics of the particular product. Typically, an active ingredient or combination thereof is present in a total concentration of at least about 0.001% by weight of the composition, such as in a range from about 0.001% to about 20%. In some embodiments, the active ingredient or combination of active ingredients is present in a concentration from about 0.1% w/w to about 10% by weight, such as, e.g., from about 0.5% w/w to about 10%, from about 1% to about 10%, from about 1% to about 5% by weight, based on the total weight of the composition. In some embodiments, the active ingredient or combination of active ingredients is present in a concentration of from about 0.001%, about 0.01%, about 0.1% , or about 1%, up to about 20% by weight, such as, e.g., from about 0.001%, about 0.002%, about 0.003%, about 0.004%, about 0.005%, about 0.006%, about 0.007%, about 0.008%, about 0.009%, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% by weight, based on the total weight of the composition. Further suitable ranges for specific active ingredients are provided herein below.

Botanical

In some embodiments, the active ingredient comprises a botanical ingredient. As used herein, the term "botanical ingredient" or "botanical" refers to any plant material or fungal-derived material, including plant material in its natural form and plant material derived from natural plant materials, such as extracts or isolates from plant materials or treated plant materials (e.g., plant materials subjected to heat treatment, fermentation, bleaching, or other treatment processes capable of altering the physical and/or chemical nature of the material). For the purposes of the present disclosure, a "botanical" includes, but is not limited to, "herbal materials," which refer to seed-producing plants that do not develop persistent woody tissue and are often valued for their medicinal or sensory characteristics (e.g., teas or tisanes). Reference to botanical material as "non-tobacco" is intended to exclude tobacco materials (i.e., does not include any Nicotiana species). In some embodiments, the compositions as disclosed herein can be characterized as free of any tobacco material (e.g., any embodiment as disclosed herein may be completely or substantially free of any tobacco material). By "substantially free" is meant that no tobacco material has been intentionally added. For example, certain embodiments can be characterized as having less than 0.001% by weight of tobacco, or less than 0.0001%, or even 0% by weight of tobacco.

When present, a botanical is typically at a concentration of from about 0.01% w/w to about 10% by weight, such as, e.g., from about 0.01% w/w, about 0.05%, about 0.1%, or about 0.5%, to about 1%, about 2%, about 3%, about 4%, about 5%, about 6%, about 7%, about 8%, about 9%, or about 10%, about 11%, about 12%, about 13%, about 14%, or about 15% by weight, based on the total weight of the composition.

The botanical materials useful in the present disclosure may comprise, without limitation, any of the compounds and sources set forth herein, including mixtures thereof. Certain botanical materials of this type are sometimes referred to as dietary supplements, nutraceuticals, "phytochemicals" or "functional foods." Certain botanicals, as the plant material or an extract thereof, have found use in traditional herbal medicine, and are described further herein. Non-limiting examples of botanicals or botanical-derived materials include ashwagandha, *Bacopa monniera*, baobab, basil, *Centella asiatica*, Chai-hu, chamomile, cherry blossom, chlorophyll, cinnamon, citrus, cloves, cocoa, cordyceps, curcumin, damiana, *Dorstenia arifolia, Dorstenia odorata*, essential oils, eucalyptus, fennel, *Galphimia glauca*, ginger, *Ginkgo biloba*, ginseng (e.g., *Panax ginseng*), green tea, *Griffonia simplicifolia*, guarana, cannabis, hemp, hops, jasmine, *Kaempferia parviflora* (Thai ginseng), kava, lavender, lemon balm, lemongrass, licorice, lutein, maca, matcha, Nardostachys chinensis, oil-based extract of *Viola odorata*, peppermint, quercetin, resveratrol, *Rhizoma gastrodiae, Rhodiola, rooibos*, rose essential oil, rosemary, *Sceletium tortuosum*, Schisandra, Skullcap, spearmint extract, Spikenard, terpenes, tisanes, turmeric, *Turnera aphrodisiaca*, valerian, white mulberry, and *Yerba mate*.

In some embodiments, the active ingredient comprises lemon balm. Lemon balm (*Melissa officinalis*) is a mildly lemon-scented herb from the same family as mint (Lamiaceae). The herb is native to Europe, North Africa, and West Asia. The tea of lemon balm, as well as the essential oil and the extract, are used in traditional and alternative medicine. In some embodiments, the active ingredient comprises lemon balm extract. In some embodiments, the lemon balm extract is present in an amount of from about 1 to about 4% by weight, based on the total weight of the composition.

In some embodiments, the active ingredient comprises ginseng. Ginseng is the root of plants of the genus *Panax*, which are characterized by the presence of unique steroid saponin phytochemicals (ginsenosides) and gintonin. Ginseng finds use as a dietary supplement in energy drinks or herbal teas, and in traditional medicine. Cultivated species include Korean ginseng (*P. ginseng*), South China ginseng (*P. notoginseng*), and American ginseng (*P. quinquefolius*). American ginseng and Korean ginseng vary in the type and quantity of various ginsenosides present. In some embodiments, the ginseng is American ginseng or Korean ginseng. In specific embodiments, the active ingredient comprises Korean ginseng. In some embodiments, ginseng is present in an amount of from about 0.4 to about 0.6% by weight, based on the total weight of the composition.

Stimulants

In some embodiments, the active ingredient comprises one or more stimulants. As used herein, the term "stimulant" refers to a material that increases activity of the central nervous system and/or the body, for example, enhancing focus, cognition, vigor, mood, alertness, and the like. Non-limiting examples of stimulants include caffeine, theacrine, theobromine, and theophylline. Theacrine (1,3,7,9-tetramethylwic acid) is a purine alkaloid which is structurally related to caffeine, and possesses stimulant, analgesic, and anti-inflammatory effects. Present stimulants may be natural, naturally derived, or wholly synthetic. For example, certain botanical materials (guarana, tea, coffee, cocoa, and the like) may possess a stimulant effect by virtue of the presence of e.g., caffeine or related alkaloids, and accordingly are "natural" stimulants. By "naturally derived" is meant the stimulant (e.g., caffeine, theacrine) is in a purified form, outside its natural (e.g., botanical) matrix. For example, caffeine can be obtained by extraction and purification from botanical sources (e.g., tea). By "wholly synthetic", it is meant that the stimulant has been obtained by chemical synthesis. In some embodiments, the active ingredient comprises caffeine. In some embodiments, the caffeine is present in an encapsulated form. On example of an encapsulated caffeine is Vitashure®, available from Balchem Corp., 52 Sunrise Park Road, New Hampton, N.Y., 10958.

When present, a stimulant or combination of stimulants (e.g., caffeine, theacrine, and combinations thereof) is typically at a concentration of from about 0.1% w/w to about 15% by weight, such as, e.g., from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 11%, about 12%, about 13%, about 14%, or about 15% by weight, based on the total weight of the composition. In some embodiments, the composition comprises caffeine in an amount of from about 1.5 to about 6% by weight, based on the total weight of the composition;

Amino Acids

In some embodiments, the active ingredient comprises an amino acid. As used herein, the term "amino acid" refers to an organic compound that contains amine (—NH$_2$) and carboxyl (—COOH) or sulfonic acid (SO$_3$H) functional groups, along with a side chain (R group), which is specific to each amino acid. Amino acids may be proteinogenic or non-proteinogenic. By "proteinogenic" is meant that the amino acid is one of the twenty naturally occurring amino acids found in proteins. The proteinogenic amino acids include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. By "non-proteinogenic" is meant that either the amino acid is not found naturally in protein, or is not directly produced by cellular machinery (e.g., is the product of post-tranlational modification). Non-limiting examples of non-proteinogenic amino acids include gamma-aminobutyric acid (GABA), taurine (2-aminoethanesulfonic acid), theanine (L-γ-glutamylethylamide), hydroxyproline, and beta-alanine. In some embodiments, the active ingredient comprises theanine. In some embodiments, the active ingredient comprises GABA. In some embodiments, the active ingredient comprises a combination of theanine and GABA. In some embodiments, the active ingredient is a combination of theanine, GABA, and lemon balm. In some embodiments, the active ingredient is a combination of caffeine, theanine, and ginseng. In some embodiments, the active ingredient comprises taurine. In some embodiments, the active ingredient is a combination of caffeine and taurine.

Without being bound by any theory of operation, it is believed that certain amino acids, such as theanine, tryptophan, GABA, or taurine, can have beneficial impact on mood, anxiety level, focus, or cognitive performance, particularly when combined with other active ingredients, such as caffeine or certain botanicals.

When present, an amino acid or combination of amino acids (e.g., theanine, taurine, GABA, tryptophan, and combinations thereof) is typically at a concentration of from about 0.01% w/w to about 15% by weight, such as, e.g., from about from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 11%, about 12%, about 13%, about 14%, or about 15% by weight, based on the total weight of the composition.

In one embodiment, the at least one active ingredient comprises tryptophan in an amount by weight from about 0.03% to about 1%, or from about 0.05% to about 0.5%.

Vitamins

In some embodiments, the active ingredient comprises a vitamin or combination of vitamins. As used herein, the term "vitamin" refers to an organic molecule (or related set of molecules) that is an essential micronutrient needed for the proper functioning of metabolism in a mammal. There are thirteen vitamins required by human metabolism, which are: vitamin A (as all-trans-retinol, all-trans-retinyl-esters, as well as all-trans-beta-carotene and other provitamin A carotenoids), vitamin B1 (thiamine), vitamin B2 (riboflavin), vitamin B3 (niacin), vitamin B5 (pantothenic acid), vitamin B6 (pyridoxine), vitamin B7 (biotin), vitamin B9 (folic acid or folate), vitamin B12 (cobalamins), vitamin C (ascorbic acid), vitamin D (calciferols), vitamin E (tocopherols and tocotrienols), and vitamin K (quinones). In some embodiments, the active ingredient comprises vitamin C. In some embodiments, the active ingredient is a combination of vitamin C, caffeine, and taurine.

When present, a vitamin or combination of vitamins (e.g., vitamin B6, vitamin B12, vitamin E, vitamin C, or a combination thereof) is typically at a concentration of from about 0.0001% to about 6% by weight, such as, e.g., from about 0.0001, about 0.001, about 0.01%, about 0.02%, about 0.03%, about 0.04%, about 0.05%, about 0.06%, about 0.07%, about 0.08%, about 0.09%, or about 0.1% w/w, to about 0.2%, about 0.3%, about 0.4%, about 0.5%, about 0.6%, about 0.7%, about 0.8%, about 0.9%, about 1%, about 2%, about 3%, about 4%, about 5% , or about 6% by weight, based on the total weight of the composition.

In some embodiments, the active ingredient comprises vitamin B6 in an amount from about 0.008% to about 0.06% by weight, or from about 0.01% to about 0.04% by weight.

In some embodiments, the active ingredient comprises vitamin B12 in an amount from about 0.0001% to about 0.007% by weight, or from about 0.0005% to about 0.001% by weight.

In some embodiments, the active ingredient comprises a combination of vitamin B6 and vitamin B12 in a total amount by weight from about 0.008% to about 0.07%.

Antioxidants

In some embodiments, the active ingredient comprises one or more antioxidants. As used herein, the term "antioxidant" refers to a substance which prevents or suppresses oxidation by terminating free radical reactions, and may delay or prevent some types of cellular damage. Antioxidants may be naturally occurring or synthetic. Naturally occurring antioxidants include those found in foods and botanical materials. Non-limiting examples of antioxidants include certain botanical materials, vitamins, polyphenols, and phenol derivatives.

Examples of botanical materials which are associated with antioxidant characteristics include without limitation acai berry, alfalfa, allspice, annatto seed, apricot oil, basil, bee balm, wild bergamot, black pepper, blueberries, borage seed oil, bugleweed, cacao, calamus root, catnip, catuaba, cayenne pepper, chaga mushroom, chervil, cinnamon, dark chocolate, potato peel, grape seed, ginseng, gingko biloba, Saint John's Wort, saw palmetto, green tea, black tea, black cohosh, cayenne, chamomile, cloves, cocoa powder, cranberry, dandelion, grapefruit, honeybush, echinacea, garlic, evening primrose, feverfew, ginger, goldenseal, hawthorn, hibiscus flower, jiaogulan, kava, lavender, licorice, marjoram, milk thistle, mints (menthe), oolong tea, beet root, orange, oregano, papaya, pennyroyal, peppermint, red clover, rooibos (red or green), rosehip, rosemary, sage, clary sage, savory, spearmint, spirulina, slippery elm bark, sorghum bran hi-tannin, sorghum grain hi-tannin, sumac bran, comfrey leaf and root, goji berries, gutu kola, thyme, turmeric, uva ursi, valerian, wild yam root, wintergreen, yacon root, yellow dock, yerba mate, yerba santa, bacopa monniera, withania somnifera, Lion's mane, and silybum marianum. Such botanical materials may be provided in fresh or dry form, essential oils, or may be in the form of an extracts. The botanical materials (as well as their extracts) often include compounds from various classes known to provide antioxidant effects, such as minerals, vitamins, isoflavones, phytoesterols, allyl sulfides, dithiolthiones, isothiocyanates, indoles, lignans, flavonoids, polyphenols, and carotenoids. Examples of compounds found in botanical extracts or oils include ascorbic acid, peanut endocarb, resveratrol, sulforaphane, beta-carotene, lycopene, lutein, co-enzyme Q, carnitine, quercetin, kaempferol, and the like. See, e.g., Santhosh et al., Phytomedicine, 12(2005) 216-220, which is incorporated herein by reference.

Non-limiting examples of other suitable antioxidants include citric acid, Vitamin E or a derivative thereof, a tocopherol, epicatechol, epigallocatechol, epigallocatechol gallate, erythorbic acid, sodium erythorbate, 4-hexylresorcinol, theaflavin, theaflavin monogallate A or B, theaflavin digallate, phenolic acids, glycosides, quercitrin, isoquercitrin, hyperoside, polyphenols, catechols, resveratrols, oleuropein, butylated hydroxyanisole (BHA), butylated hydroxytoluene (BHT), tertiary butylhydroquinone (TBHQ), and combinations thereof.

When present, an antioxidant is typically at a concentration of from about 0.001% w/w to about 10% by weight, such as, e.g., from about 0.001%, about 0.005%, about 0.01% w/w, about 0.05%, about 0.1%, or about 0.5%, to about 1%, about 2%, about 3%, about 4%, about 5%, about 6%, about 7%, about 8%, about 9%, or about 10%, based on the total weight of the composition.

Nicotine Component

In certain embodiments, the active ingredient comprises a nicotine component. By "nicotine component" is meant any suitable form of nicotine (e.g., free base or salt) for providing oral absorption of at least a portion of the nicotine present. Typically, the nicotine component is selected from the group consisting of nicotine free base and a nicotine salt. In some embodiments, the nicotine component is nicotine in its free base form, which easily can be adsorbed in for example, a microcrystalline cellulose material to form a microcrystalline cellulose-nicotine carrier complex. See, for example, the discussion of nicotine in free base form in US Pat. Pub. No. 2004/0191322 to Hansson, which is incorporated herein by reference.

In some embodiments, at least a portion of the nicotine component can be employed in the form of a salt. Salts of nicotine can be provided using the types of ingredients and techniques set forth in U.S. Pat. No. 2,033,909 to Cox et al. and Perfetti, *Beitrage Tabakforschung Int.*, 12: 43-54 (1983), which are incorporated herein by reference. Additionally, salts of nicotine are available from sources such as Pfaltz and Bauer, Inc. and K&K Laboratories, Division of ICN Biochemicals, Inc. Typically, the nicotine component is selected from the group consisting of nicotine free base, a nicotine salt such as hydrochloride, dihydrochloride, monotartrate, bitartrate, sulfate, salicylate, and nicotine zinc chloride.

In some embodiments, at least a portion of the nicotine can be in the form of a resin complex of nicotine, where nicotine is bound in an ion-exchange resin, such as nicotine polacrilex, which is nicotine bound to, for example, a polymethacrilic acid, such as Amberlite IRP64, Purolite C115HMR, or Doshion P551. See, for example, U.S. Pat. No. 3,901,248 to Lichtneckert et al., which is incorporated herein by reference. Another example is a nicotine-polyacrylic carbomer complex, such as with Carbopol 974P. In some embodiments, nicotine may be present in the form of a nicotine polyacrylic complex.

Typically, the nicotine component (calculated as the free base) when present, is in a concentration of at least about 0.001% by weight of the composition, such as in a range from about 0.001% to about 10%. In some embodiments, the nicotine component is present in a concentration from about 0.1% w/w to about 10% by weight, such as, e.g., from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, or about 10% by weight, calculated as the free base and based on the total weight of the composition. In some embodiments, the nicotine component is present in a concentration from about 0.1% w/w to about 3% by weight, such as, e.g., from about 0.1% w/w to about 2.5%, from about 0.1% to about 2.0%, from about 0.1% to about 1.5%, or from about 0.1% to about 1% by weight, calculated as the free base and based on the total weight of the composition.

In some embodiments, the products or compositions of the disclosure can be characterized as free of any nicotine component (e.g., any embodiment as disclosed herein may be completely or substantially free of any nicotine component). By "substantially free" is meant that no nicotine has been intentionally added, beyond trace amounts that may be naturally present in e.g., a botanical material. For example, certain embodiments can be characterized as having less than 0.001% by weight of nicotine, or less than 0.0001%, or even 0% by weight of nicotine, calculated as the free base.

In some embodiments, the active ingredient comprises a nicotine component (e.g., any product or composition of the disclosure, in addition to comprising any active ingredient or combination of active ingredients as disclosed herein, may further comprise a nicotine component).

Cannabinoids

In some embodiments, the active ingredient comprises one or more cannabinoids. As used herein, the term "cannabinoid" refers to a class of diverse chemical compounds that acts on cannabinoid receptors, also known as the endocannabinoid system, in cells that alter neurotransmitter release in the brain. Ligands for these receptor proteins include the endocannabinoids produced naturally in the body by animals; phytocannabinoids, found in cannabis; and synthetic cannabinoids, manufactured artificially. Cannabinoids found in cannabis include, without limitation: cannabigerol (CBG), cannabichromene (CBC), cannabidiol (CBD), tetrahydrocannabinol (THC), cannabinol (CBN), cannabinodiol (CBDL), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabinerolic acid, cannabidiolic acid (CBDA), cannabinol propyl variant (CBNV), cannabitriol (CBO), tetrahydrocannabinolic acid (THCA), and tetrahydrocannabivarinic acid (THCV A). In certain embodiments, the cannabinoid is selected from tetrahydrocannabinol (THC), the primary psychoactive compound in cannabis, and cannabidiol (CBD) another major constituent of the plant, but which is devoid of psychoactivity. All of the above compounds can be used in the form of an isolate from plant material or synthetically derived.

Alternatively, the active ingredient can be a cannabimimetic, which is a class of compounds derived from plants other than cannabis that have biological effects on the endocannabinoid system similar to cannabinoids. Examples include yangonin, alpha-amyrin or beta-amyrin (also classified as terpenes), cyanidin, curcumin (tumeric), catechin, quercetin, salvinorin A, N-acylethanolamines, and N-alkylamide lipids.

When present, a cannabinoid (e.g., CBD) or cannabimimetic is typically in a concentration of at least about 0.1% by weight of the composition, such as in a range from about 0.1% to about 30%, such as, e.g., from about 0.1%, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 15%, about 20%, or about 30% by weight, based on the total weight of the composition.

Terpenes

Active ingredients suitable for use in the present disclosure can also be classified as terpenes, many of which are associated with biological effects, such as calming effects. Terpenes are understood to have the general formula of $(C_5H_8)n$ and include monoterpenes, sesquiterpenes, and diterpenes. Terpenes can be acyclic, monocyclic or bicyclic in structure. Some terpenes provide an entourage effect when used in combination with cannabinoids or cannabimimetics. Examples include beta-caryophyllene, linalool, limonene, beta-citronellol, linalyl acetate, pinene (alpha or beta), geraniol, carvone, eucalyptol, menthone, iso-menthone, piperitone, myrcene, beta-bourbonene, and germacrene, which may be used singly or in combination.

Pharmaceutical Ingredients

In some embodiments, the active ingredient comprises an active pharmaceutical ingredient (API). The API can be any known agent adapted for therapeutic, prophylactic, or diagnostic use. These can include, for example, synthetic organic compounds, proteins and peptides, polysaccharides and other sugars, lipids, phospholipids, inorganic compounds (e.g., magnesium, selenium, zinc, nitrate), neurotransmitters or precursors thereof (e.g., serotonin, 5-hydroxytryptophan, oxitriptan, acetylcholine, dopamine, melatonin), and nucleic acid sequences, having therapeutic, prophylactic, or diagnostic activity. Non-limiting examples of APIs include analgesics and antipyretics (e.g., acetylsalicylic acid, acetaminophen, 3-(4-isobutylphenyl)propanoic acid), phosphatidylserine, myoinositol, docosahexaenoic acid (DHA, Omega-3), arachidonic acid (AA, Omega-6), S-adenosylmethionine (SAM), beta-hydroxy-beta-methylbutyrate (HMB), citicoline (cytidine-5'-diphosphate-choline), and cotinine. In some embodiments, the active ingredient comprises citicoline. In some embodiments, the active ingredient is a combination of citicoline, caffeine, theanine, and ginseng. In some embodiments, the active ingredient comprises sunflower lecithin. In some embodiments, the active ingredient is a combination of sunflower lecithin, caffeine, theanine, and ginseng.

The amount of API may vary. For example, when present, an API is typically at a concentration of from about 0.001% w/w to about 10% by weight, such as, e.g., from about 0.01%, about 0.02%, about 0.03%, about 0.04%, about 0.05%, about 0.06%, about 0.07%, about 0.08%, about 0.09%, about 0.1% w/w, about 0.2%, about 0.3%, about 0.4%, about 0.5% about 0.6%, about 0.7%, about 0.8%, about 0.9%, or about 1%, to about 2%, about 3%, about 4%, about 5%, about 6%, about 7%, about 8%, about 9%, or about 10% by weight, based on the total weight of the composition.

In some embodiments, the composition is substantially free of any API. By "substantially free of any API" means that the composition does not contain, and specifically excludes, the presence of any API as defined herein, such as any Food and Drug Administration (FDA) approved therapeutic agent intended to treat any medical condition.

Advantageously, in some embodiments, the compositions and products of the present disclosure (irrespective of their physical form, e.g., a pastille-type product or a lozenge-type product) may provide the active ingredient(s) contained therein (e.g., nicotine) in relatively low amounts when compared to traditional smokeless tobacco products commonly known in the art. It should be noted that embodiments particularly including nicotine in relatively low amounts advantageously provides compositions and products having a more desirable delivery profile of active nicotine and improved organoleptic properties when those products are inserted into the oral cavity of a user of those products. For example, oral products of the present disclosure may exhibit improved flavor characteristics, improved appearance (e.g., translucency or transparency), and improved mouthfeel when compared to traditional smokeless tobacco products having higher amounts of nicotine or tobacco materials incorporated therein. Such improvements are achieved by providing oral products with lower amounts of active ingredients therein. For example, the compositions and products as described herein may comprise an active ingredient in the form of a nicotine component in an amount of less than about 2 weight percent, based on the total weight of the composition. In some embodiments, the oral product may comprise a nicotine component in an amount of less than about 2 weight percent, less than about 1.75 weight percent, less than about 1.5 weight percent, less than about 1.25 weight percent, less than about 1.0 weight percent, less than about 0.75 weight percent, less than about 0.50 weight percent, or less than about 0.25 weight percent, based on the total weight of the composition.

Tobacco Material

In some embodiments, oral products according to the present disclosure may further comprise a tobacco material. The tobacco material can vary in species, type, and form. Generally, the tobacco material is obtained from for a harvested plant of the *Nicotiana* species. Example *Nicotiana* species include *N. tabacum, N. rustica, N. alata, N. arentsii, N. excelsior, N. forgetiana, N. glauca, N. glutinosa, N. gossei, N. kawakamii, N. knightiana, N. langsdorffi, N. otophora, N. setchelli, N. sylvestris, N. tomentosa, N. tomentosiformis, N. undulata, N. x sanderae, N. africana, N. amplexicaulis, N. benavidesii, N. bonariensis, N. debneyi, N. longiflora, N. maritina, N. megalosiphon, N. occidentalis, N. paniculata, N. plumbaginifolia, N. raimondii, N. rosulata, N. simulans, N. stocktonii, N. suaveolens, N. umbratica, N. velutina, N. wigandioides, N. acaulis, N. acuminata, N. attenuata, N. benthamiana, N. cavicola, N. clevelandii, N. cordifolia, N. corymbosa, N. fragrans, N. goodspeedii, N. linearis, N. miersii, N. nudicaulis, N. obtusifolia, N. occidentalis* subsp. *Hersperis, N. pauciflora, N. petunioides, N. quadrivalvis, N. repanda, N. rotundifolia, N. solanifolia,* and *N. spegazzinii*. Various representative other types of plants from the *Nicotiana* species are set forth in Goodspeed, *The Genus Nicotiana*, (Chonica Botanica) (1954); U.S. Pat. No. 4,660,577 to Sensabaugh, Jr. et al.; U.S. Pat. No. 5,387,416 to White et al., U.S. Pat. No. 7,025,066 to Lawson et al.; U.S. Pat. No. 7,798,153 to Lawrence, Jr. and U.S. Pat. No. 8,186,360 to Marshall et al.; each of which is incorporated herein by reference. Descriptions of various types of tobaccos, growing practices and harvesting practices are set forth in *Tobacco Production, Chemistry and Technology*, Davis et al. (Eds.) (1999), which is incorporated herein by reference.

*Nicotiana* species from which suitable tobacco materials can be obtained can be derived using genetic-modification or crossbreeding techniques (e.g., tobacco plants can be genetically engineered or crossbred to increase or decrease production of components, characteristics or attributes). See, for example, the types of genetic modifications of plants set forth in U.S. Pat. No. 5,539,093 to Fitzmaurice et al.; U.S. Pat. No. 5,668,295 to Wahab et al.; U.S. Pat. No. 5,705,624 to Fitzmaurice et al.; U.S. Pat. No. 5,844,119 to Weigl; U.S.

Pat. No. 6,730,832 to Dominguez et al.; U.S. Pat. No. 7,173,170 to Liu et al.; U.S. Pat. No. 7,208,659 to Colliver et al. and U.S. Pat. No. 7,230,160 to Benning et al.; US Patent Appl. Pub. No. 2006/0236434 to Conkling et al.; and PCT WO2008/103935 to Nielsen et al. See, also, the types of tobaccos that are set forth in U.S. Pat. No. 4,660,577 to Sensabaugh, Jr. et al.; U.S. Pat. No. 5,387,416 to White et al.; and U.S. Pat. No. 6,730,832 to Dominguez et al., each of which is incorporated herein by reference.

The *Nicotiana* species can, in some embodiments, be selected for the content of various compounds that are present therein. For example, plants can be selected on the basis that those plants produce relatively high quantities of one or more of the compounds desired to be isolated therefrom. In certain embodiments, plants of the *Nicotiana* species (e.g., *Galpao commun* tobacco) are specifically grown for their abundance of leaf surface compounds. Tobacco plants can be grown in greenhouses, growth chambers, or outdoors in fields, or grown hydroponically.

Various parts or portions of the plant of the *Nicotiana* species can be included within the compositions as disclosed herein. For example, virtually all of the plant (e.g., the whole plant) can be harvested, and employed as such. Alternatively, various parts or pieces of the plant can be harvested or separated for further use after harvest. For example, the flower, leaves, stem, stalk, roots, seeds, and various combinations thereof, can be isolated for further use or treatment. In some embodiments, the tobacco material comprises tobacco leaf (lamina). The compositions disclosed herein can include processed tobacco parts or pieces, cured and aged tobacco in essentially natural lamina and/or stem form, a tobacco extract, extracted tobacco pulp (e.g., using water as a solvent), or a mixture of the foregoing (e.g., a mixture that combines extracted tobacco pulp with granulated cured and aged natural tobacco lamina).

In certain embodiments, the tobacco material comprises solid tobacco material selected from the group consisting of lamina and stems. The tobacco that is used for the mixture most preferably includes tobacco lamina, or a tobacco lamina and stem mixture (of which at least a portion is smoke-treated). Portions of the tobaccos within the mixture may have processed forms, such as processed tobacco stems (e.g., cut-rolled stems, cut-rolled-expanded stems or cut-puffed stems), or volume expanded tobacco (e.g., puffed tobacco, such as dry ice expanded tobacco (DIET)). See, for example, the tobacco expansion processes set forth in U.S. Pat. No. 4,340,073 to de la Burde et al.; U.S. Pat. No. 5,259,403 to Guy et al.; and U.S. Pat. No. 5,908,032 to Poindexter, et al.; and U.S. Pat. No. 7,556,047 to Poindexter, et al., all of which are incorporated by reference. In addition, the d mixture optionally may incorporate tobacco that has been fermented. See, also, the types of tobacco processing techniques set forth in PCT WO2005/063060 to Atchley et al., which is incorporated herein by reference.

The tobacco material is typically used in a form that can be described as particulate (i.e., shredded, ground, granulated, or powder form). The manner by which the tobacco material is provided in a finely divided or powder type of form may vary. Preferably, plant parts or pieces are comminuted, ground or pulverized into a particulate form using equipment and techniques for grinding, milling, or the like. Most preferably, the plant material is relatively dry in form during grinding or milling, using equipment such as hammer mills, cutter heads, air control mills, or the like. For example, tobacco parts or pieces may be ground or milled when the moisture content thereof is less than about 15 weight percent or less than about 5 weight percent. Most preferably, the tobacco material is employed in the form of parts or pieces that have an average particle size between 1.4 millimeters and 250 microns. In some instances, the tobacco particles may be sized to pass through a screen mesh to obtain the particle size range required. If desired, air classification equipment may be used to ensure that small sized tobacco particles of the desired sizes, or range of sizes, may be collected. If desired, differently sized pieces of granulated tobacco may be mixed together.

The manner by which the tobacco is provided in a finely divided or powder type of form may vary. Preferably, tobacco parts or pieces are comminuted, ground or pulverized into a powder type of form using equipment and techniques for grinding, milling, or the like. Most preferably, the tobacco is relatively dry in form during grinding or milling, using equipment such as hammer mills, cutter heads, air control mills, or the like. For example, tobacco parts or pieces may be ground or milled when the moisture content thereof is less than about 15 weight percent to less than about 5 weight percent. For example, the tobacco plant or portion thereof can be separated into individual parts or pieces (e.g., the leaves can be removed from the stems, and/or the stems and leaves can be removed from the stalk). The harvested plant or individual parts or pieces can be further subdivided into parts or pieces (e.g., the leaves can be shredded, cut, comminuted, pulverized, milled or ground into pieces or parts that can be characterized as filler-type pieces, granules, particulates or fine powders). The plant, or parts thereof, can be subjected to external forces or pressure (e.g., by being pressed or subjected to roll treatment). When carrying out such processing conditions, the plant or portion thereof can have a moisture content that approximates its natural moisture content (e.g., its moisture content immediately upon harvest), a moisture content achieved by adding moisture to the plant or portion thereof, or a moisture content that results from the drying of the plant or portion thereof. For example, powdered, pulverized, ground or milled pieces of plants or portions thereof can have moisture contents of less than about 25 weight percent, often less than about 20 weight percent, and frequently less than about 15 weight percent.

For the preparation of oral products, it is typical for a harvested plant of the *Nicotiana* species to be subjected to a curing process. The tobacco materials incorporated within the compositions for inclusion within products as disclosed herein are those that have been appropriately cured and/or aged. Descriptions of various types of curing processes for various types of tobaccos are set forth in *Tobacco Production, Chemistry and Technology,* Davis et al. (Eds.) (1999). Examples of techniques and conditions for curing flue-cured tobacco are set forth in Nestor et al., *Beitrage Tabakforsch. Int,* 20, 467-475 (2003) and U.S. Pat. No. 6,895,974 to Peele, which are incorporated herein by reference. Representative techniques and conditions for air curing tobacco are set forth in U.S. Pat. No. 7,650,892 to Groves et al.; Roton et al., *Beitrage Tabakforsch. Int.,* 21, 305-320 (2005) and Staaf et al., *Beitrage Tabakforsch. Int.,* 21, 321-330 (2005), which are incorporated herein by reference. Certain types of tobaccos can be subjected to alternative types of curing processes, such as fire curing or sun curing.

In certain embodiments, tobacco materials that can be employed include flue-cured or Virginia (e.g., K326), burley, sun-cured (e.g., Indian Kurnool and Oriental tobaccos, including Katerini, Prelip, Komotini, Xanthi and Yambol tobaccos), Maryland, dark, dark-fired, dark air cured (e.g., Madole, Passanda, Cubano, Jatin and Bezuki tobaccos), light air cured (e.g., North Wisconsin and Galpao tobaccos), Indian air cured, Red Russian and *Rustica* tobaccos, as well as various other rare or specialty tobaccos and various blends of any of the foregoing tobaccos.

The tobacco material may also have a so-called "blended" form. For example, the tobacco material may include a mixture of parts or pieces of flue-cured, burley (e.g., Malawi burley tobacco) and Oriental tobaccos (e.g., as tobacco composed of, or derived from, tobacco lamina, or a mixture of tobacco lamina and tobacco stem). For example, a representative blend may incorporate about 30 to about 70 parts burley tobacco (e.g., lamina, or lamina and stem), and about 30 to about 70 parts flue cured tobacco (e.g., stem, lamina, or lamina and stem) on a weight basis. Other example tobacco blends incorporate about 75 parts flue-cured tobacco, about 15 parts burley tobacco, and about 10 parts Oriental tobacco; or about 65 parts flue-cured tobacco, about 25 parts burley tobacco, and about 10 parts Oriental tobacco; or about 65 parts flue-cured tobacco, about 10 parts burley tobacco, and about 25 parts Oriental tobacco; on a weight basis. Other example tobacco blends incorporate about 20 to about 30 parts Oriental tobacco and about 70 to about 80 parts flue-cured tobacco on a weight basis.

Tobacco materials used in the present disclosure can be subjected to, for example, fermentation, bleaching, and the like. If desired, the tobacco materials can be, for example, irradiated, pasteurized, or otherwise subjected to controlled heat treatment. Such treatment processes are detailed, for example, in U.S. Pat. No. 8,061,362 to Mua et al., which is incorporated herein by reference. In certain embodiments, tobacco materials can be treated with water and an additive capable of inhibiting reaction of asparagine to form acrylamide upon heating of the tobacco material (e.g., an additive selected from the group consisting of lysine, glycine, histidine, alanine, methionine, cysteine, glutamic acid, aspartic acid, proline, phenylalanine, valine, arginine, compositions incorporating di- and trivalent cations, asparaginase, certain non-reducing saccharides, certain reducing agents, phenolic compounds, certain compounds having at least one free thiol group or functionality, oxidizing agents, oxidation catalysts, natural plant extracts (e.g., rosemary extract), and combinations thereof. See, for example, the types of treatment processes described in US Pat. Pub. Nos. 8,434,496, 8,944,072, and 8,991,403 to Chen et al., which are all incorporated herein by reference. In certain embodiments, this type of treatment is useful where the original tobacco material is subjected to heat in the processes previously described.

At least a portion of the tobacco material employed in the tobacco composition or product can have the form of an extract. In some embodiments, all of the tobacco material employed in the tobacco composition or product may be in the form of an extract, e.g., such as a tobacco-derived nicotine extract. Tobacco extracts can be obtained by extracting tobacco using a solvent having an aqueous character such as distilled water or tap water. As such, aqueous tobacco extracts can be provided by extracting tobacco with water, such that water insoluble pulp material is separated from the aqueous solvent and the water soluble and dispersible tobacco components dissolved and dispersed therein. The tobacco extract can be employed in a variety of forms. For example, the aqueous tobacco extract can be isolated in an essentially solvent free form, such as can be obtained as a result of the use of a spray drying or freeze drying process, or other similar types of processing steps. Alternatively, the aqueous tobacco extract can be employed in a liquid form, and as such, the content of tobacco solubles within the liquid solvent can be controlled by selection of the amount of solvent employed for extraction, concentration of the liquid tobacco extract by removal of solvent, addition of solvent to dilute the liquid tobacco extract, or the like. Example techniques for extracting components of tobacco are described in U.S. Pat. No. 4,144,895 to Fiore; U.S. Pat. No. 4,150,677 to Osborne, Jr. et al.; U.S. Pat. No. 4,267,847 to Reid; U.S. Pat. No. 4,289,147 to Wildman et al.; U.S. Pat. No. 4,351,346 to Brummer et al.; U.S. Pat. No. 4,359,059 to Brummer et al.; U.S. Pat. No. 4,506,682 to Muller; U.S. Pat. No. 4,589,428 to Keritsis; U.S. Pat. No. 4,605,016 to Soga et al.; U.S. Pat. No. 4,716,911 to Poulose et al.; U.S. Pat. No. 4,727,889 to Niven, Jr. et al.; U.S. Pat. No. 4,887,618 to Bernasek et al.; U.S. Pat. No. 4,941,484 to Clapp et al.; U.S. Pat. No. 4,967,771 to Fagg et al.; U.S. Pat. No. 4,986,286 to Roberts et al.; U.S. Pat. No. 5,005,593 to Fagg et al.; U.S. Pat. No. 5,018,540 to Grubbs et al.; U.S. Pat. No. 5,060,669 to White et al.; U.S. Pat. No. 5,065,775 to Fagg; U.S. Pat. No. 5,074,319 to White et al.; U.S. Pat. No. 5,099,862 to White et al.; U.S. Pat. No. 5,121,757 to White et al.; U.S. Pat. No. 5,131,414 to Fagg; U.S. Pat. No. 5,131,415 to Munoz et al.; U.S. Pat. No. 5,148,819 to Fagg; U.S. Pat. No. 5,197,494 to Kramer; U.S. Pat. No. 5,230,354 to Smith et al.; U.S. Pat. No. 5,234,008 to Fagg; U.S. Pat. No. 5,243,999 to Smith; U.S. Pat. No. 5,301,694 to Raymond et al.; U.S. Pat. No. 5,318,050 to Gonzalez-Parra et al.; U.S. Pat. No. 5,343,879 to Teague; U.S. Pat. No. 5,360,022 to Newton; U.S. Pat. No. 5,435,325 to Clapp et al.; U.S. Pat. No. 5,445,169 to Brinkley et al.; U.S. Pat. No. 6,131,584 to Lauterbach; U.S. Pat. No. 6,284,875 to Turpen et al.; U.S. Pat. No. 6,298,859 to Kierulff et al.; U.S. Pat. No. 6,772,767 to Mua et al.; U.S. Pat. No. 6,817,970 to Bent et al.; U.S. Pat. No. 6,906,172 to Bratcher et al.; U.S. Pat. No. 7,034,128 to Turpen et al.; U.S. Pat. No. 7,048,211 to Bratcher et al.; and U.S. Pat. No. 7,337,782 to Thompson, all of which are incorporated by reference herein.

According to the present disclosure, the *Nicotiana* plant or portion thereof (as described herein above) is typically subjected to processing intended to provide improved clarity of the tobacco material. In certain embodiments, the tobacco material used in the products of the invention is in the form of an extract, such as an aqueous extract of a tobacco material. Improved clarity of a tobacco extract can be obtained, for example, by removing high molecular weight components from the tobacco extract. In certain embodiments, high molecular weight components that are beneficially removed according to the present invention include, but are not limited to, high molecular weight Maillard browning polymers, proteins, polysaccharides, certain pigments, and bacteria. Various methods can be used for this purpose, including size exclusion chromatography, microfiltration, ultrafiltration, nanofiltration, reverse osmosis, and combinations thereof. Ideally, the tobacco extract may undergo an ultrafiltration process in order to provide an ultrafiltered tobacco extract. Example filters, methods and processes for ultrafiltration of tobacco materials are set forth in U.S. Pat. No. 9,084,439 to Holton Jr. and U.S. Pat. No. 9,901,113 to Holton Jr.; the entirety of which are incorporated herein by reference.

According to the present disclosure, the ultrafiltration process is designed to achieve a tobacco extract having a decreased level of suspended solids, and thus an increased level of clarity. For example, depending on the molecular weight cutoff of the filters, the ultrafiltered extract may comprise only compounds with molecular weights below about 50,000, below about 25,000, below about 10,000 Da, below about 7,500 Da, below about 5,000 Da, below about 2,500 Da, or below about 1,000 Da. The ultrafiltered extract typically comprises primarily sugars, nicotine, and amino acids.

The ultrafiltered extract exhibits a level of improvement in clarity over the non-ultrafiltered extract. Clarity of the extract, and oral products incorporating such extracts according to the present disclosure, is typically defined in terms of translucency. As used herein, "translucent" or "translucency" refers to materials allowing some level of light to travel therethrough diffusely. In certain embodiments, certain materials of the invention (e.g., certain tobacco extracts or final smokeless tobacco products made therefrom) can have such a high degree of clarity that the material can be classified as "transparent" or exhibiting "transparency," which is defined as a material allowing light to pass freely through without significant diffusion. The clarity of the ultrafiltered extract is such that there is some level of translucency as opposed to opacity (which refers to materials that are impenetrable by light).

The improvement in clarity of the ultrafiltered extract over the non-ultrafiltered extract can be quantified by any known method. For example, optical methods such as turbidimetry (or nephelometry) and colorimetry may be used to quantify the cloudiness (light scattering) and the color (light absorption), respectively, of the ultrafiltered extract or products made therefrom.

Translucency can also be confirmed by visual inspection by simply holding the material (e.g., extract) or product up to a light source and determining if light travels through the material or product in a diffuse manner.

In certain embodiments, the ultrafiltered extract is analyzed by contacting the extract with light and measuring the percent of light that has not been absorbed and/or dispersed by the extract. The measurement can be done, for example, using a standard spectrophotometer at a given wavelength. The spectrophotometer is typically calibrated with deionized water, which is assigned a transparency value of 100%. Acceptable levels of translucency/transparency at a given wavelength in the ultrafiltered extract can vary. Typically, the ultrafiltered extract has a translucency of greater than about 5%, greater than about 10%, greater than about 15%, greater than about 20%, greater than about 25%, greater than about 30%, greater than about 40%, greater than about 50%, greater than about 60%, greater than about 60%, greater than about 70%, greater than about 80%, or greater than about 90%. Typically, the ultrafiltered extract will not be colorless, and will have some discernible brown/black coloring. Following ultrafiltration, the extract can be stored in the refrigerator or freezer or the extract can be freeze dried or spray dried prior to use in the products of the invention. In certain embodiments, it is provided in syrup form.

Although in some embodiments, the tobacco extract is used directly, it may be desirable to heat treat the extract. This thermal treatment can be conducted before the ultrafiltration, after the ultrafiltration, or both before and after the ultrafiltration. For example, a tobacco material can be thermally processed by mixing the tobacco material, water, and an additive selected from the group consisting of lysine, glycine, histidine, alanine, methionine, glutamic acid, aspartic acid, proline, phenylalanine, valine, arginine, di- and trivalent cations, asparaginase, saccharides, phenolic compounds, reducing agents, compounds having a free thiol group, oxidizing agents (e.g., hydrogen peroxide), oxidation catalysts, plant extracts, and combinations thereof, to form a moist tobacco mixture; and heating the moist tobacco mixture at a temperature of at least about 60° C. to form a heat-treated tobacco mixture. In one embodiment, the treated tobacco extract is heat treated in the presence of water, NaOH, and an additive (e.g., lysine) at about 88° C. for about 60 minutes. Such heat treatment can help prevent acrylamide production resulting from reaction of asparagine with reducing sugars in tobacco materials and can provide some degree of pasteurization. See, for example, US Pat. Pub. No. 2010/0300463 to Chen et al., which is incorporated herein by reference. In certain embodiments wherein a heat-treated tobacco extract is used in a smokeless tobacco product of the present invention, the product can be characterized by very low acrylamide content. For example, in some embodiments, the smokeless tobacco product is characterized by an acrylamide content of less than about 500 ppb (ng/g), less than about 400 ppb, less than about 300 ppb, less than about 200 ppb, or less than about 100 ppb.

Accordingly, "treated tobacco extract" as used herein refers to a tobacco extract that has been treated in some way to remove high molecular weight components and thereby improve clarity (e.g., an ultrafiltered extract). The "treated tobacco extract" may or may not be heat-treated as described herein.

It should be noted that inclusion of a tobacco material into the compositions and products described herein is meant to be optional and is not required. In some embodiments, oral products as described herein can generally be characterized as being tobacco free-alternatives. For example, in some embodiments, oral products of the present disclosure may be said to be completely free or substantially free of tobacco material (other than purified nicotine as an active ingredient). Oral products that are referred to as "completely free of" or "substantially free of" a tobacco material herein are meant to refer to oral products that can be characterized as having less than about 1.0% by weight, less than about 0.5% by weight, less than about 0.1% by weight of tobacco material, or 0% by weight of tobacco material.

Buffering Agent and/or pH Adjuster

In some embodiments, the products of the present disclosure may further comprise one or more buffering agents and/or pH adjusters (i.e., acids or bases). In such embodiments, the one or more buffering agents and/or pH adjusters are added to the mixture to ensure that the final oral product has a pH within a desirable range. Example pH ranges for oral products as described herein are generally from about 5 to about 7. In such embodiments, the amount of buffering agent and/or pH adjuster added to the product mixture is simply that amount required to bring the formulation to or keep the formulation at the desired pH. The amount of buffering agent and/or pH adjuster added to any given formulation can be readily calculated by one skilled in the art based on the desired pH and may comprise, for example, about 0.5% to about 1% by weight of the mixture. In some embodiments, the quantity of pH adjuster present may vary based on the acidity and basicity of other components which may be present in the composition (e.g., nicotine, salts, buffers, and the like). Accordingly, the buffering agent and/or pH adjuster is provided in a quantity sufficient to provide a pH of the composition of from about 5.0 to about 7.0, for example, from about 5.0, about 5.5, or about 6.0, to about 6.5, or about 7.0. In some embodiments, the organic acid is provided in a quantity sufficient to provide a pH of the composition of from about 5.5 to about 6.5, for example, from about 5.5, about 5.6, about 5.7, about 5.8, about 5.9, or about 6.0, to about 6.1, about 6.2, about 6.3, about 6.4, or about 6.5.

It should be noted that the pH level of the oral products may be varied to alter certain characteristics of the product, for example, the release profile of the active ingredient contained within the product. For example, in some embodiments, an amount of buffering agent (e.g., such as a citric acid) may be incorporated into the product so as to alter the overall pH of that product to be between about 5.0 and 7.0, as noted above. Preferably, in some embodiments, the pH may be adjusted to a pH of approximately 5.5. Advantageously, it was discovered that adding citric acid to adjust the pH of the products described herein to a pH of around 5.5 generally reduced the nicotine loss in those products when compared to products having higher pH values, such as those commonly employed in traditional smokeless tobacco products (e.g., in the range of about 7 to about 11, or preferably about 8 to about 10). In some embodiments, the citric acid may be used as a processing aid which is added to the composition or product to reduce nicotine loss during the production thereof. The use of citric acid in the products disclosed herein is not meant to be limiting and it should be noted that any buffering agent and/or pH adjuster may be suitable for altering the pH of the overall product. Such buffering agents and/or pH adjusters may be added singularly, or in the form of a combination of one or more compounds.

Additionally, various food-grade buffering agents are known and can be used to adjust the pH of the products as described herein. Suitable buffering agents may include those selected from the group consisting of acetates, glycinates, phosphates, glycerophosphates, citrates such as citrates of alkaline metals, carbonates, hydrogen carbonates, and borates, and mixtures thereof. In certain embodiments, the buffering agent is an amino acid, as taught for example, in US Pat. Pub. No. 2008/0286341 to Andersson et al. and PCT Appl. No. WO2008/040371 to Andersson et al., which are both incorporated herein by reference. As noted therein, various amino acids and salts thereof are useful for this purpose, including, but not limited to, arginine, asparagine, glutamic acid, glutamine, glycine, histidine, isoleucine, leucine, lysine, methionine, phenylalanine, serine, threonine, valine, cysteic acid, N-glycylglycine, and ornithine. In certain embodiments, N-glycylglycine or L-lysine is added as a buffering agent. In some embodiments, an amino acid buffering agent is used in combination with another amino acid buffering agent and/or in combination with one or more non-amino acid buffering agents. In certain embodiments, the optional pH adjusting agent is a base (e.g., NaOH). In certain embodiments, L-lysine and NaOH are added to the compositions of the present invention.

Emulsifier

In certain embodiments, an emulsifier may be added. In certain embodiments, lecithin can be added to the composition to provide smoother textural properties of the composition and to improve flowability and mixing of the lipid with the remaining components of the composition. Lecithin can be used in an amount of about 0.01 to about 5% by dry weight of the composition, such as about 0.1 to about 2.5% or about 0.1 to about 1.0%.

Further Additives

In addition to the components provided in the lozenge and pastille compositions as noted above, such compositions may further comprise one or more additives. For example, lozenge and pastille compositions according to the present disclosure may further comprise one or more of a flavoring agent, one or more sweeteners, one or more additional binders, disintegration aids, humectants, salts, and mixtures thereof.

As used herein, a "flavorant" or "flavoring agent" is any flavorful or aromatic substance capable of altering the sensory characteristics associated with the oral products of the present disclosure. Example sensory characteristics that can be modified by the flavorant include, taste, mouthfeel, moistness, coolness/heat, and/or fragrance/aroma. Non-limiting examples of flavoring agents that may be included within the present compositions and/or products can include vanilla, coffee, chocolate/cocoa, cream, mint, spearmint, menthol, peppermint, wintergreen, eucalyptus, lavender, cardamom, nutmeg, cinnamon, clove, cascarilla, sandalwood, honey, jasmine, ginger, anise, sage, licorice, lemon, orange, apple, peach, lime, cherry, strawberry, trigeminal sensates, terpenes, and any combinations thereof. See also, Leffingwell et al., Tobacco Flavoring for Smoking Products, R. J. Reynolds Tobacco Company (1972), which is incorporated herein by reference. Flavoring agents may comprise components such as terpenes, terpenoids, aldehydes, ketones, esters, and the like. In some embodiments, the flavoring agent is a trigeminal sensate. As used herein, "trigeminal sensate" refers to a flavoring agent which has an effect on the trigeminal nerve, producing sensations including heating, cooling, tingling, and the like. Non-limiting examples of trigeminal sensate flavoring agents include capsaicin, citric acid, menthol, Sichuan buttons, erythritol, and cubebol. Flavorings also may include components that are considered moistening, cooling or smoothening agents, such as eucalyptus. These flavors may be provided neat (i.e., alone) or in a composite, and may be employed as concentrates or flavor packages (e.g., spearmint and menthol, orange and cinnamon; lime, pineapple, and the like). Representative types of components also are set forth in U.,S. Pat. No. 5,387,416 to White et al.; US Pat. App. Pub. No. 2005/0244521 to Strickland et al.; and PCT Application Pub. No. WO 05/041699 to Quinter et al., each of which is incorporated herein by reference. In some instances, the flavoring agent may be provided in a spray-dried form or a liquid form.

The flavoring agent generally comprises at least one volatile flavor component. As used herein, "volatile" refers to a chemical substance that forms a vapor readily at ambient temperatures (i.e., a chemical substance that has a high vapor pressure at a given temperature relative to a nonvolatile substance). Typically, a volatile flavor component has a molecular weight below about 400 Da, and often include at least one carbon-carbon double bond, carbon-oxygen double bond, or both. In one embodiment, the at least one volatile flavor component comprises one or more alcohols, aldehydes, aromatic hydrocarbons, ketones, esters, terpenes, terpenoids, or a combination thereof. Non-limiting examples of aldehydes include vanillin, ethyl vanillin, p-anisaldehyde, hexanal, furfural, isovaleraldehyde, cuminaldehyde, benzaldehyde, and citronellal. Non-limiting examples of ketones include 1-hydroxy-2-propanone and 2-hydroxy-3-methyl-2-cyclopentenone-1-one. Non-limiting examples of esters include allyl hexanoate, ethyl heptanoate, ethyl hexanoate, isoamyl acetate, and 3-methylbutyl acetate. Non-limiting examples of terpenes include sabinene, limonene, gamma-terpinene, beta-farnesene, nerolidol, thujone, myrcene, geraniol, nerol, citronellol, linalool, and eucalyptol. In one embodiment, the at least one volatile flavor component comprises one or more of ethyl vanillin, cinnamaldehyde, sabinene, limonene, gamma-terpinene, beta-farnesene, or citral. In one embodiment, the at least one volatile flavor component comprises ethyl vanillin. Flavorants are typically present in an amount of about 0.5 to about 10 weight percent, often about 1 to about 6 weight percent, and most often about 2 to about 5 weight percent, based on the total weight of the composition.

Sweeteners can be used in natural or artificial form or as a combination of artificial and natural sweeteners. Examples of natural sweeteners include fructose, sucrose, glucose, maltose, mannose, galactose, lactose, isomaltulose, stevia, honey, and the like. Examples of artificial sweeteners include sucralose, maltodextrin, saccharin, aspartame, acesulfame K, neotame and the like. In one embodiment, sucrose and sucralose are primary sweetener ingredients. When present, a representative amount of sweetener, whether an artificial sweetener and/or natural sugar, may make up at least about 0.2 percent or at least about 5 percent, of the total weight of the composition. Preferably, the amount of sweetener within the composition will not exceed about 40 percent, often will not exceed about 35 percent, and frequently will not exceed about 30 percent, of the total weight of the composition. Sucrose can be particularly advantageous in certain embodiments as an ingredient as it is believed to contribute to the chewing resistance or "bounce" of the final product. In addition, while granulated sucrose provides far less sweetening effect as compared to sucralose, the presence of sucrose can be advantageous as an additional filler component. When these two sweeteners are present together, the sucralose is typically present in an amount of at least about 0.25 weight percent, often at least about 0.5 weight percent, and most often at least about 1.0 weight percent (e.g., about 0.25 to about 2.0 weight percent), and the sucrose is typically present in an amount of at least about 2.0 weight percent, often at least about 3.0 weight percent, and most often at least about 4.0 weight percent (e.g., about 1.0 to about 6.0 weight percent). In further embodiments, sucralose is present in an amount of about 0.01 to about 0.5 weight percent (e.g., about 0.02 to about 0.1 weight percent).

A salt (e.g., sodium chloride, flour salt) may be employed in amounts sufficient to provide desired sensory attributes to the products of the present disclosure. Non-limiting examples of suitable salts include sodium chloride, potassium chloride, ammonium chloride, flour salt, and the like. When present, a representative amount of salt is at least about 0.5 weight percent or at least about 1.0 weight percent or at least about 1.5 weight percent, but will typically may make up less than about 5 percent of the total weight of the composition (e.g., about 0.5 to about 4 weight percent).

A humectant (e.g., glycerin) may be employed in amounts sufficient to provide desired moisture attributes to the oral products described herein. Further, in some instances, the humectant may impart desirable flow characteristics to the smokeless tobacco composition for depositing in a starch mold. When present, a representative amount of humectant is at least about 0.5 weight percent or at least about 1.0 weight percent or at least about 1.5 weight percent, but will typically make up less than about 5 percent of the total weight of the composition (e.g., about 0.5 to about 4 weight percent).

An additional binder (or combination of binders) may be employed in certain embodiments, in amounts sufficient to provide the desired physical attributes and physical integrity to the mixture, and binders also often function as thickening or gelling agents. Typical binders can be organic or inorganic, or a combination thereof. Representative binders include povidone, sodium alginate, starch-based binders, pectin, carrageenan, pullulan, zein, and the like, and combinations thereof. In some embodiments, the binder comprises pectin or carrageenan or combinations thereof. The amount of binder utilized in the composition can vary, but is typically up to about 30 weight percent, and certain embodiments are characterized by a binder content of at least about 0.1% by weight, such as about 1 to about 30% by weight, or about 5 to about 10% by weight, based on the total weight of the composition.

In some embodiments, the lozenge and/or pastille products described herein may include one or more colorants. A colorant may be employed in amounts sufficient to provide the desired physical attributes to the composition or product. Examples of colorants include various dyes and pigments, such as caramel coloring and titanium dioxide. The amount of colorant utilized in the compositions or products can vary, but when present is typically up to about 3 weight percent, such as from about 0.1%, about 0.5%, or about 1%, to about 3% by weight, based on the total weight of the composition.

Various other substances can be added to the compositions of the present invention. For example, excipients such as fillers or carriers for active ingredients (e.g., calcium polycarbophil, microcrystalline cellulose, hydroxypropylcellulose, sodium carboxymethylcellulose, cornstarch, silicon dioxide, calcium carbonate, lactose, and starches including potato starch, maize starch, etc.), thickeners, film formers and binders (e.g., hydroxypropyl cellulose, hydroxypropyl methylcellulose, acacia, sodium alginate, xanthan gum and gelatin), antiadherents (e.g., talc), glidants (e.g., colloidal silica), humectants (e.g., glycerin), preservatives and antioxidants (e.g., sodium benzoate and ascorbyl palmitate), surfactants (e.g., polysorbate 80), dyes or pigments (e.g., titanium dioxide or D&C Yellow No. 10), and lubricants or processing aids (e.g., calcium stearate or magnesium stearate) are added to the compositions in certain embodiments. Examples of even further types of additives that may be used in the present compositions and products include thickening or gelling agents (e.g., fish gelatin), emulsifiers, oral care additives (e.g., thyme oil, eucalyptus oil, and zinc), preservatives (e.g., potassium sorbate and the like), disintegration aids, zinc or magnesium salts selected to be relatively water soluble for compositions with greater water solubility (e.g., magnesium or zinc gluconate) or selected to be relatively water insoluble for compositions with reduced water solubility (e.g., magnesium or zinc oxide), or combinations thereof. See, for example, those representative components, combination of components, relative amounts of those components, and manners and methods for employing those components, set forth in U.S. Pat. No. 9,237,769 to Mua et al., U.S. Pat. No. 7,861,728 to Holton, Jr. et al., U.S. Pat. App. Pub. No. 2010/0291245 to Gao et al., and U.S. Pat. App. Pub. No. 2007/0062549 to Holton, Jr. et al., each of which is incorporated herein by reference. Typical inclusion ranges for such additional additives can vary depending on the nature and function of the additive and the intended effect on the final mixture, with an example range of up to about 10% by weight, based on total weight of the mixture (e.g., about 0.1 to about 5% by weight).

In some embodiments, the composition comprises a magnesium salt. A non-limiting example of a suitable magnesium salt is magnesium gluconate. In some embodiments, the composition comprises magnesium in an amount by weight from about 0.1% to about 2%, or from about 0.2 to about 1%, based on elemental magnesium.

The aforementioned types of additives can be employed together (e.g., as additive formulations) or separately (e.g., individual additive components can be added at different stages involved in the preparation of the final oral product). The relative amounts of the various components within the oral products may vary, and typically are selected so as to provide the desired sensory and performance characteristics to the oral product. Furthermore, the aforementioned types of additives may be encapsulated as provided in the final product or composition. Example encapsulated additives are described, for example, in WO 2010/132444 A2 to Atchley, which has been previously incorporated by reference herein.

The manner by which the various components of the lozenge and pastille compositions referenced above are combined may vary. The various components of those compositions may be contacted, combined, or mixed together in conical-type blenders, mixing drums, ribbon blenders, or the like, such as a Hobart mixer. As such, the overall mixture of various components with the active ingredient may be relatively uniform in nature. See also, for example, the types of methodologies set forth in U.S. Pat. No. 4,148,325 to Solomon et al.; U.S. Pat. No. 6,510,855 to Korte et al.; and U.S. Pat. No. 6,834,654 to Williams, each of which is incorporated herein by reference.

Methods of Manufacturing Pastille Products

Representative pastille compositions and products may incorporate about 10 weight percent or less of at least one active ingredient, about 0.01 to about 2 percent sweetener, about 0.1 to about 5 percent humectant, about 25 to about 45 percent of at least one sugar alcohol filler, about 35 to about 55 percent of at least one gum, about 0.1 to about 5 percent of at least one flavoring agent, and about 0.1 to about 5 percent of a salt, based on the total weight of the product. The particular percentages and choice of ingredients will vary depending upon the desired flavor, texture, and other characteristics.

The manners and methods used to formulate and manufacture a pastille product as described herein above can vary. For example, the compositions forming the pastille products are prepared such that the mixture thereof may be used in a starch molding process for forming the pastille product. Example pastille production processes are set forth in U.S. Pat. No. 4,725,440 to Ridgway et al and U.S. Pat. No. 6,077,524 to Bolder et al., which are incorporated by reference herein. In some embodiments, the compositions for forming the pastille products may be prepared such that the mixture thereof may be used in a starchless molding process (e.g., not including a starch-based component in the molding process) for forming the pastille product.

In one embodiment, the process comprises heating a gum, and optionally hydrating that gum component with water, and then stirring at least one active ingredient into the heated gum component. Generally, the gum may be heated to a temperature in the range of about 60° C. to about 80° C. for a period of a few seconds to a few minutes. In some embodiments, the gum may be heated to a temperature of about 71° C. before stirring in the at least one active ingredient, to allow the at least active ingredient to dissolve therein. In some instances, an aqueous mixture is formed in a separate container by mixing one or more additives (e.g., such as salts, sweeteners, humectants, emulsifiers, flavoring agents, and others) with water to form the aqueous mixture. Then, the aqueous mixture may be admixed with the heated gum (including the at least one active ingredient that has been added therein) to form a mixture in the form of a slurry.

In some embodiments, the at least one sugar alcohol component may be added separately to this mixture, or, in other embodiments, the at least one sugar alcohol may be combined with the gum and the active ingredient prior to addition to the mixture. In some instances, the at least one sugar alcohol may be heated in yet another separate container and added to the mixture separately. For example, in some embodiments, the at least one sugar alcohol (which may optionally include isomalt/maltitol/erythritol) may be heated to a temperature in the range of about 160° C. to about 190° C. before addition to the mixture. In some embodiments, the at least one sugar alcohol may be heated to a temperature of at least about 160° C., at least about 170° C., at least about 180° C., or at least about 190° C. In some instances, the heated sugar alcohol may be allowed to cool to a temperature in the range of about 120° C. to about 160° C. prior to addition to the mixture. In some embodiments, for example, the heated sugar alcohol may be cooled to a temperature of about 160° C. or less, about 150° C. or less, about 140° C. or less, or about 130° C. or less prior to addition to the mixture.

In some instances, the heated (and optionally cooled) sugar alcohol may be combined with the mixture (e.g., including the heated gum, the at least one active ingredient, and the aqueous mixture) and stirred using a high shear mixer or a Hobart mixing bowl with a whipping attachment to provide a pastille composition, which may also be in the form of a slurry. The pastille composition may then be heated to an elevated temperature for a period of time, for example, heated to between about 40° C. to about 80° C., and typically heated to about 71° C., for a period of about 1 to about 3 minutes, for example, to dissolve any dry ingredient within the pastille composition. The heating step can be characterized as heating at a temperature of at least about 50° C., at least about 60° C., or at least about 70° C. The pastille composition typically has a moisture content of at least about 40 percent by weight water, based on the total weight of the composition.

According to some aspects, the pastille composition, in the form of a slurry, may optionally be put through a deaerating step or process prior to being received in a mold or being subjected to other processing steps, so as to reduce or eliminate air bubbles present in the slurry mixture. Air bubbles entrapped within the slurry may affect the final weight of the pastille product, which could lead to a lack of weight uniformity between units of the final product. As such, any deaerating methods and systems may be employed for removing such air bubbles from the slurry material. For example, the slurry may be placed under reduced pressure (i.e., below atmospheric pressure) to pull the air bubbles out of the slurry mixture. In some instances, a vacuum deaerating process may be employed in which the slurry mixture is placed in a vacuum deaerator for deaerating the slurry mixture using pressure reduction. In some instances, the slurry mixture may be under vacuum for about 1 to about 10 minutes, and typically for about 3 to about 5 minutes. The deaerating step may be observed and adjusted accordingly in order to controllably remove the gaseous components from the slurry mixture.

The viscosity of the heated and deaerated slurry mixture may be measured using, for example, a Brookfield viscometer HA Series, SC4 water jacket, 27/13R sample chamber and a No. 27 spindle. The pastille composition may have a viscosity of about 5.7 Pascal-seconds (Pa·s) to about 6.2 Pa·s when heated to a temperature of about 38° C., about 4.9 Pa·s to about 5.4 Pa·s when heated to a temperature of about 43° C., and about 4.2 Pa·s to about 4.7 Pa·s when heated to a temperature of about 50° C. In some instances, extra water may be added to the pastille composition so as to provide a desired viscosity thereof.

Once the desired viscosity is achieved, the heated pastille composition may then be deposited into a mold, such as, for example, a starch mold. While the process as further described herein is directed to forming a pastille product using a starch mold, it is noted that other types of molds may be used in the process, such as, for example, starchless molds, pectin molds, plastic tray molds, metallic tray molds, neoprene tray molds, etc.

In instances involving the use of starch molds, the starch molds may be pre-dried to remove moisture content from the starch mold itself. That is, prior to receiving the slurry or viscous pastille composition, the starch mold may be subjected to an elevated temperature to drive out moisture in the starch mold. For example, in some instances, the starch mold may initially have a moisture content of about 10-15 weight percent. Such levels of moisture could potentially have an effect on the uniformity of the resultant product. In this regard, certain moisture levels in the starch mold could potentially have a wrinkling or pruning effect on the product such that the final product has a shriveled or otherwise wrinkled appearance. As such, the starch mold may be dried at an elevated temperature to reduce the moisture content of the starch mold to between about 4 and about 10 weight percent, and preferably between about 6 and about 8 weight percent, based on the total weight of the starch mold. By taking such steps, the product may, in some instances, be more uniformly consistent in appearance. Furthermore, the starch mold may be heated to an elevated temperature prior to receiving the pastille composition such that the starch mold itself is at an elevated temperature when receiving the pastille composition.

The pastille composition remains in the starch mold at an elevated temperature such as, for example, at between about 40° C. to about 80° C. (e.g., at least about 40° C. or at least about 50° C.), and typically at about 60° C. The pastille composition may be held at the elevated temperature for a predetermined duration of time such as, for example, about 15-48 hours, and typically about 24 hours, so as to allow the pastille composition to cure and solidify into pastille form, while driving the moisture content of the pastille composition to a desired final moisture level. As noted above, in some embodiments, the desired final moisture level of the pastille product may be within the range of about 5 to about 25 weight percent, or about 8 to about 20 weight percent, or about 10 to about 15 weight percent, based on the total weight of the product unit. In this regard, curing generally refers to the solidification process in which moisture loss occurs, the viscosity of the composition is raised, and chemical and physical changes begin to occur (e.g., crystallization, cross-linking, gelling, film forming, etc.). The pastille composition is allowed to cool and thereafter removed from the starch mold. In some instances, the pastille composition may be allowed to cool at refrigerated or below ambient temperatures. An air blower/shaker device can be used to remove starch remnants from the pastille composition after being removed from the starch mold.

The pastille composition is then allowed to post-cure for a time and at a temperature suitable to allow the composition to become equilibrated to a desired moisture, shape and form. The time and temperature can vary without departing from the invention and depend in part on the desired final characteristics of the product. In one embodiment, the post-cure is conducted at ambient temperature for at least about 20 hours after being removed from the mold. The resultant pastille product may be provided in individual pieces weighing between about 0.5 grams to about 5 grams, although aspects of the present disclosure are not limited to such weights.

The curing times and temperatures of the pastille composition can be varied as desired. In this regard, such variables may affect the final visual appearance of the pastille product. For example, extended curing times and/or low curing temperatures may affect the final outer configuration or contours of the pastille product. That is, the rate of drying and/or curing of the product can affect the final properties of the product. In some instances, for example, lowering the curing temperature and extending the curing time may cause the pastille product to have a relatively smooth outer surface. In contrast, curing at higher temperatures for shorter period of times can lead to a roughened or wrinkled appearance in the product.

According to other aspects of the present disclosure, rather than using molds to prepare the pastille product, an extrusion process may be employed in which the final pastille product is extruded. In some instances, the pastille composition in slurry form may be formed into a sheet and allowed to dry to a moisture content, for example, of about 15 percent to about 25 percent by weight water to form a tacky or otherwise pasty material, which is in a form capable of physical handling. The material may then be chopped or otherwise cut into smaller pieces using, for example, a mixer. The chopped material may then be extruded through an extrusion device to any shape/size desired, including shapes that may be difficult or impossible to achieve with a mold. In some instances, the extruded product may then be dried to achieve a desired moisture content. A similar type process is described, for example, in U.S. Pat. No. 3,806,617 to Smylie et al., which is incorporated herein by reference in its entirety. Further, the pastille composition may be subjected to a co-extrusion process with another composition.

Shapes such as, for example, rods and cubes can be formed by first extruding the material through a die having the desired cross-section (e.g., round or square) and then optionally cutting the extruded material into desired lengths. Techniques and equipment for extruding tobacco materials are set forth in U.S. Pat. No. 3,098,492 to Wursburg; U.S. Pat. No. 4,874,000 to Tamol et al.; U.S. Pat. No. 4,880,018 to Graves et al.; U.S. Pat. No. 4,989,620 to Keritsis et al.; U.S. Pat. No. 5,072,744 to Luke et al.; U.S. Pat. No. 5,829,453 to White et al.; and U.S. Pat. No. 6,182,670 to White et al.; each of which is incorporated herein by reference. Example extrusion equipment suitable for use include food or gum extruders, or industrial pasta extruders such as Model TP 200/300 available from Emiliomiti, LLC of Italy. In some instances, a single machine may be capable of achieving multiple steps of the processes described herein, such as, for example, kneader systems available from Buss AG.

The pastille product can be provided in any suitable predetermined shape or form, and most preferably is provided in the form having a general shape of a pill, pellet, tablet, coin, bead, ovoid, obloid, cube, or the like. The mouthfeel of the smokeless tobacco product preferably has a slightly chewable and dissolvable quality with a mild resilience or "bounce" upon chewing that gradually leads to greater malleability during use. According to one aspect, the pastille product is preferably capable of lasting in the user's mouth for about 10-15 minutes until it completely dissolves. Preferably, the products do not, to any substantial degree, leave any residue in the mouth of the user thereof, and do not impart a slick, waxy, or slimy sensation to the mouth of the user.

According to some embodiments, the pastille composition may be coated with a coating substance after being removed from the starch mold and prior to drying. For example, a glazing or anti-sticking coating substance, such as, for example, CAPOL 410 (available from Centerchem, Inc.), may be applied to the pastille composition to provide free-flowing properties. Outer coatings can also help to improve storage stability of the pastille products of the present disclosure as well as improve the packaging process by reducing friability and dusting. Devices for providing outer coating layers to the products of the present disclosure include pan coaters and spray coaters, and particularly include the coating devices available as CompuLab 24, CompuLab 36, Accela-Cota 48 and Accela-Cota 60 from Thomas Engineering.

An example outer coating comprises a film-forming polymer, such as a cellulosic polymer, an optional plasticizer, and optional flavorants, colorants, salts, sweeteners or other additives of the types set forth herein. The coating compositions are usually aqueous in nature and can be applied using any pellet or tablet coating technique known in the art, such as pan coating. Example film-forming polymers include cellulosic polymers such as methylcellulose, hydroxypropyl cellulose (HPC), hydroxypropyl methylcellulose (HPMC), hydroxyethyl cellulose, and carboxy methylcellulose. Example plasticizers include aqueous solutions or emulsions of glyceryl monostearate and triethyl citrate.

In one embodiment, the coating composition comprises up to about 75 weight percent of a film-forming polymer solution (e.g., about 40 to about 70 weight percent based on total weight of the coating formulation), up to about 5 weight percent of a plasticizer (e.g., about 0.5 to about 2 weight percent), up to about 5 weight percent of a sweetener (e.g., about 0.5 to about 2 weight percent), up to about 10 weight percent of one or more colorants (e.g., about 1 to about 5 weight percent), up to about 5 weight percent of one or more flavorants (e.g., about 0.5 to about 3 weight percent), up to about 2 weight percent of a salt such as NaCl (e.g., about 0.1 to about 1 weight percent), and the balance water. Example coating compositions and methods of application are described in U.S. application Ser. No. 12/876,785 to Hunt et al.; filed Sep. 7, 2010, and which is incorporated by reference herein.

Although the foregoing description focuses on compositions that are uniform throughout each product unit, products can also be formed with multiple different formulations having different properties in the same product unit. For example, two different compositions can be deposited in a single mold to produce a layered product. Still further, two different compositions could be co-extruded to form a product with different characteristics across its cross-section. Such a process could be used to provide a product with two different compositions featuring different dissolution rates such that a first portion of the product dissolves at a first rate (e.g., a faster rate) and a second portion dissolves at a second, slower rate.

Products of the present disclosure may be packaged and stored in any suitable packaging. See, for example, the various types of containers for smokeless types of products that are set forth in U.S. Pat. Nos. 7,014,039 to Henson et al.; U.S. Pat. No. 7,537,110 to Kutsch et al.; U.S. Pat. No. 7,584,843 to Kutsch et al.; D592,956 to Thiellier and D594,154 to Patel et al.; US Pat. Pub. Nos. 2008/0173317 to Robinson et al.; 2009/0014343 to Clark et al.; 2009/0014450 to Bjorkholm; 2009/0250360 to Bellamah et al.; 2009/0266837 to Gelardi et al.; 2009/0223989 to Gelardi; 2009/0230003 to Thiellier; 2010/0084424 to Gelardi; and 2010/0133140 to Bailey et al; and U.S. patent Applicaton Ser. No. 29/342,212, filed Aug. 20, 2009, to Bailey et al.; U.S. Ser. No. 12/425,180, filed Apr. 16, 2009, to Bailey et al.; U.S. Ser. No. 12/685,819, filed Jan. 12, 2010, to Bailey et al.; and U.S. Ser. No. 12/814,015, filed Jun. 11, 2010, to Gelardi et al., which are incorporated herein by reference.

Methods of Manufacturing Lozenge Products

Representative lozenge compositions and products may incorporate about 10 weight percent or less of at least one active ingredient, about 0.01 to about 2 percent artificial sweetener, about 1 to about 5 percent humectant, about 1 to about 5 percent natural sweetener, at least about 80 percent of a sugar substitute, about 0.1 to about 10 percent of a sugar alcohol syrup, one or more flavorants in an amount of up to about 5 percent, and salt in an amount up to about 3 percent, based on the total weight of the product. The particular percentages and choice of ingredients will vary depending upon the desired flavor, texture, and other characteristics.

The manners and methods used to formulate and manufacture a lozenge product as described herein above can vary. For example, the compositions can be prepared via any method commonly used for the preparation of hard boiled confections. Example methods for the preparation of hard confections can be found, for example, in LFRA Ingredients Handbook, Sweeteners, Janet M. Dalzell, Ed., Leatherhead Food RA (December 1996), pp. 21-44, which is incorporated herein by reference.

Typically, a first mixture of ingredients is prepared. The composition of the first mixture of ingredients can vary; however, it typically comprises a sugar substitute and may contain various additional substances (e.g., the sugar alcohol syrup, NaCl, preservatives, further sweeteners, water, and/or flavorings). In certain embodiments, it comprises the sugar substitute, salt, and vanillin. In other embodiments, the first mixture comprises the sugar substitute and the sugar alcohol syrup. Typically, the first mixture of ingredients does not contain the active ingredient; although, it some embodiments, the active ingredient may be incorporated into the first mixture of ingredients.

The first mixture of ingredients is heated until it melts; subsequently, the mixture is heated to or past the hard crack stage. In confectionary making, the hard crack stage is defined as the temperature at which threads of the heated mixture (obtained by pulling a sample of cooled syrup between the thumb and forefinger) are brittle or as the temperature at which trying to mold the syrup results in cracking. According to the present method, the temperature at which the hard crack stage is achieved can vary, depending on the specific makeup of the product mixture but generally is between about 145° C. and about 170° C. Typically, the mixture is not heated above about 171° C., which is the temperature at which caramelization begins to occur. In the processes of the present disclosure, the mixture is typically heated to the hard crack stage temperature or above and then allowed to cool. The heating can be conducted at atmospheric pressure or under vacuum. Typically, the method of the present invention is conducted at atmospheric pressure.

In one example embodiment, the first mixture of ingredients comprises a high percentage of isomalt and the mixture is heated to about 143° C. Once all components are dissolved, the temperature is raised past the hard crack stage (e.g., to about 166° C.). The mixture is heated to this temperature and then removed from the heat to allow the mixture to cool.

In certain embodiments, the active ingredients and, optionally, additional components (e.g., additional sweeteners, fillers, flavorants, and water) as described above are separately combined in a second mixture. The second mixture is added to the first mixture of ingredients, typically after the first mixture of ingredients has been removed from the heat. The addition of the second mixture may, in some embodiments, occur only after the heated first mixture of ingredients has cooled to a predetermined temperature (e.g., in certain embodiments, to about 132° C.). In certain embodiments, one or more flavorants are added to the second mixture immediately prior to adding the mixture to the first, heated mixture of ingredients. Certain flavorants are volatile and are thus preferably added after the mixture has cooled somewhat.

The combined mixture is then formed into the desired shape. In certain embodiments, the mixture is poured directly into molds, formed (e.g., rolled or pressed) into the desired shape, or extruded. If desired, the mixture can be extruded or injection molded. In certain embodiments, the mixture is formed or extruded into a mold of desired shape in an enclosed system, which may require decreased temperature and which may limit evaporation of certain mixture components. For example, such a system may limit the evaporation of volatile components including, but not limited to, flavorants. Other methods of producing lozenges are also intended to be encompassed herein.

Typical conditions associated with manufacture of food grade lozenge products such as described herein include control of heat and temperature (i.e., the degree of heat to which the various ingredients are exposed during manufacture and the temperature of the manufacturing environment), moisture content (e.g., the degree of moisture present within individual ingredients and within the final composition), humidity within the manufacturing environment, atmospheric control (e.g., nitrogen atmosphere), airflow experienced by the various ingredients during the manufacturing process, and other similar types of factors. Additionally, various process steps involved in product manufacture can involve selection of certain solvents and processing aids, use of heat and radiation, refrigeration and cryogenic conditions, ingredient mixing rates, and the like. The manufacturing conditions also can be controlled due to selection of the form of various ingredients (e.g., solid, liquid, or gas), particle size or crystalline nature of ingredients of solid form, concentration of ingredients in liquid form, or the like. Ingredients can be processed into the desired composition by techniques such as extrusion, compression, spraying, and the like.

In certain embodiments, the lozenge product may be transparent or translucent. As used herein, "translucent" or "translucency" refers to materials allowing some level of light to travel therethrough diffusely. In certain embodiments, lozenge products of the present disclosure can have such a high degree of clarity that the material can be classified as "transparent" or exhibiting "transparency," which is defined as a material allowing light to pass freely through without significant diffusion. The clarity of the lozenge product is such that there is some level of translucency as opposed to opacity (which refers to materials that are impenetrable by light). Transparency/translucency can be determined by any means commonly used in the art; however, it is commonly measured by spectrophotometric light transmission over a range of wavelengths (e.g., from about 400-700 nm). Alternatively, optical methods such as turbidimetry (or nephelometry) and colorimetry may be used to quantify the cloudiness (light scattering) and the color (light absorption), respectively, of the lozenge products provided herein. Translucency can also be confirmed by visual inspection by simply holding the material (e.g., extract) or product up to a light source and determining if light travels through the product in a diffuse manner.

EXPERIMENTAL

The following examples are provided to illustrate further aspects associated with the present disclosure, but should not be construed as limiting the scope thereof. Unless otherwise noted, all parts and percentages are by dry weight.

Example 1

An oral product in the form of a pastille (referred to herein as "Pastille A") and configured for oral use is provided in the following manner.

An aqueous mixture is prepared. The aqueous mixture is formed by admixing water, a salt, a sweetener, a humectant, and a flavoring agent. Next, a gum is heated to a temperature of about 71° C. and then, the at least one active ingredient is stirred into the heated gum component. The heated gum (including the at least one active ingredient therein) is then added to the aqueous composition to form a mixture. Then, at least one sugar alcohol is heated to a temperature of about 175° C. and then cooled to a temperature of about 150° C. The cooled sugar alcohol is then added to the mixture and stirred in a Hobart mixing bowl to form a pastille composition.

The pastille composition is heated to about 71° C. and then deposited into a starch mold. The pastille composition remains in the starch mold for about 24 hours at about 60° C. The pastille composition is allowed to cool and then removed from the starch mold. The oral composition is then cured at ambient room temperature for about 24 hours to provide the pastille product configured for oral use. Table 1 below illustrates the relative percentages of each individual component in the final oral product prepared as described herein.

TABLE 1

| Pastille A | |
|---|---|
| Sugar Alcohol | 25%-45% |
| Gum | 35%-55% |
| Active Ingredient | 1%-10% |
| Humectant | 0.1%-5% |
| Salt | 0.1%-5% |
| Flavoring Agent | 0.1%-5% |
| Sweetener | 0.01%-1% |
| Water | 5%-10% |

Example 2

An oral product in the form of a pastille (referred to herein as "Pastille B") and configured for oral use is provided in the following manner.

An aqueous mixture is prepared. The aqueous mixture is formed by admixing water, a salt, a sweetener (sucralose), a humectant (glycerin), and a flavoring agent. Next, a gum (gum arabic solution) is heated to a temperature of about 71° C. and then, the at least one active ingredient (e.g., including caffeine, taurine, and ascorbic acid) is stirred into the heated gum component. The heated gum (including the at least one active ingredient therein) is then added to the aqueous composition to form a mixture. Then, the at least one sugar alcohol (e.g., including isomalt, maltitol, and erythritol) is heated to a temperature of about 175° C. and then cooled to a temperature of about 150° C. The cooled sugar alcohol is then added to the mixture and stirred in a Hobart mixing bowl to form a pastille composition and allowed to cool.

The pastille composition is heated to about 71° C. and then deposited into a starch mold. The pastille composition remains in the starch mold for about 24 hours at about 60° C. The pastille composition is allowed to cool and then removed from the starch mold. The oral composition is then cured at ambient room temperature for about 24 hours to provide the pastille product configured for oral use. Table 2 below illustrates the relative percentages of each individual component in the final oral product prepared as described herein.

TABLE 2

| Pastille B | |
|---|---|
| Isomalt | 20%-35% |
| Maltitol | 1%-10% |
| Erythritol | 0.1%-2% |
| Glycerin | 0.1%-2% |
| Water | 5%-15% |
| Salt | 1%-3% |
| Sucralose | 0.01%-1% |
| Caffeine | 1%-5% |
| Taurine | 1%-5% |
| Ascorbic Acid | 0.1%-2% |
| Flavor | 0.1%-2% |
| Gum Arabic Solution | 35%-55% |

Example 3

An oral product in the form of a pastille (referred to herein as "Pastille C") and configured for oral use is provided in the following manner.

An aqueous mixture is prepared. The aqueous mixture is formed by admixing water, a salt, a sweetener (sucralose), a humectant (glycerin), and a flavoring agent. Next, a gum (gum arabic solution) is heated to a temperature of about 71° C. and then, the at least one active ingredient (e.g., including theanine, GABA, and lemon balm) is stirred into the heated gum component. The heated gum (including the at least one active ingredient therein) is then added to the aqueous composition to form a mixture. Then, the at least one sugar alcohol (e.g., including isomalt, maltitol, and erythritol) is heated to a temperature of about 175° C. and then cooled to a temperature of about 150° C. The cooled sugar alcohol is then added to the mixture and stirred in a Hobart mixing bowl to form a pastille composition and allowed to cool.

The pastille composition is heated to about 71° C. and then deposited into a starch mold. The pastille composition remains in the starch mold for about 24 hours at about 60° C. The pastille composition is allowed to cool and then removed from the starch mold. The oral composition is then cured at ambient room temperature for about 24 hours to provide the pastille product configured for oral use. Table 3 below illustrates the relative percentages of each individual component in the final oral product prepared as described herein.

TABLE 3

| Pastille C | |
|---|---|
| Isomalt | 20%-35% |
| Maltitol | 1%-10% |
| Erythritol | 0.1%-2% |
| Glycerin | 0.1%-2% |
| Water | 5%-15% |
| Salt | 1%-3% |
| Sucralose | 0.01%-1% |
| Theanine | 1%-5% |
| GABA | 1%-5% |
| Lemon Balm | 0.1%-2% |
| Flavor | 0.1%-2% |
| Gum Arabic Solution | 35%-55% |

Example 4

An oral product in the form of a pastille (referred to herein as "Pastille D") and configured for oral use is provided in the following manner.

An aqueous mixture is prepared. The aqueous mixture is formed by admixing water, a salt, a sweetener (sucralose), a humectant (glycerin), and a flavoring agent. Next, a gum (gum arabic solution) is heated to a temperature of about 71° C. and then, the at least one active ingredient (e.g., including caffeine, theanine, and ginseng) is stirred into the heated gum component. The heated gum (including the at least one active ingredient therein) is then added to the aqueous composition to form a mixture. Then, the at least one sugar alcohol (e.g., including isomalt, maltitol, and erythritol) is heated to a temperature of about 175° C. and then cooled to a temperature of about 150° C. The cooled sugar alcohol is then added to the mixture and stirred in a Hobart mixing bowl to form a pastille composition and allowed to cool.

The pastille composition is heated to about 71° C. and then deposited into a starch mold. The pastille composition remains in the starch mold for about 24 hours at about 60° C. The pastille composition is allowed to cool and then removed from the starch mold. The oral composition is then cured at ambient room temperature for about 24 hours to provide the pastille product configured for oral use. Table 4 below illustrates the relative percentages of each individual component in the final oral product prepared as described herein.

TABLE 4

| Pastille D | |
|---|---|
| Isomalt | 20%-35% |
| Maltitol | 1%-10% |
| Erythritol | 0.1%-2% |
| Glycerin | 0.1%-2% |
| Water | 5%-15% |
| Salt | 1%-3% |
| Sucralose | 0.01%-1% |
| Caffeine | 1%-5% |
| Theanine | 1%-5% |
| Ginseng | 0.1%-2% |
| Flavor | 0.1%-2% |
| Gum Arabic Solution | 35%-55% |

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. An oral product, the oral product comprising at least one active ingredient in an amount of about 10 percent or less by weight, at least one sugar alcohol in an amount from about 25% to about 45% by weight, and a gum in an amount from about 35% to about 55% by weight, based on the total weight of the product, the product being in the form of a pastille,
wherein the oral product is free of a tobacco material.

2. The oral product of claim 1, wherein the at least one active ingredient is selected from the group consisting of a botanicals, nutraceuticals, stimulants, amino acids, vitamins, cannabinoids, cannabimimetics, terpenes, and combinations thereof.

3. The oral product of claim 1, wherein the at least one active ingredient is selected from the group consisting of caffeine, taurine, GABA, theanine, tryptophan, vitamin B6, vitamin B12, vitamin C, lemon balm extract, ginseng, citicoline, sunflower lecithin, and combinations thereof.

4. The oral product of claim 3, wherein the at least one active ingredient comprises a combination of caffeine, taurine, and ascorbic acid.

5. The oral product of claim 4, wherein the caffeine is present in an amount of about 2% to about 4% by weight, the taurine is present in an amount of about 2% to about 4% by weight, and the ascorbic acid is present in an amount of about 1% to about 3% by weight, based on the total weight of the product.

6. The oral product of claim 3, wherein the at least one active ingredient comprises theanine, gamma-aminobutyric acid, and optionally lemon balm.

7. The oral product of claim 6, wherein the theanine is present in an amount of about 2% to about 4% by weight, the gamma-aminobutyric acid is present in an amount of about 2% to about 4% by weight, and the lemon balm is present in an amount of about 1% to about 3% by weight, based on the total weight of the product.

8. The oral product of claim 3, wherein the at least one active ingredient comprises caffeine, theanine, and optionally ginseng.

9. The oral product of claim 8, wherein the caffeine is present in an amount of about 2% to about 4%, the theanine is present in an amount of about 2% to about 4% by weight, and the ginseng is present in an amount of about 0.1% to about 1% by weight, based on the total weight of the product.

10. The oral product of claim 3, wherein the at least one active ingredient comprises:
theanine;
theanine and tryptophan; or
theanine and vitamin B6, vitamin B12, or both.

11. The oral product of claim 10, comprising theanine and one or both of vitamins B6 and vitamin B12.

12. The oral product of claim 1, wherein the at least one active ingredient is present in the range of about 6% to about 8% by weight based on the total weight of the product.

13. The oral product of claim 1, wherein the oral product is free of nicotine or a nicotine-derived component.

14. The oral product of claim 1, wherein the at least one sugar alcohol is selected from the group consisting of erythritol, arabitol, ribitol, isomalt, maltitol, dulcitol, iditol, mannitol, xylitol, lactitol, sorbitol, and combinations thereof.

15. The oral product of claim 14, wherein the least one sugar alcohol is selected from the group consisting of isomalt, maltitol, erythritol, and combinations thereof.

16. The oral product of claim 15, wherein the at least one sugar alcohol comprises isomalt in an amount from about 20% to about 35% by weight, maltitol in an amount from about 1% to about 10% by weight, and erythritol in an amount from about 0.1% to about 2% by weight, based on the total weight of the product.

17. The oral product of claim 1, wherein the gum is selected from the group consisting of gum arabic, xanthan gum, guar gum, ghatti gum, gum tragacanth, karaya gum, locust bean gum, gellan gum, and combinations thereof.

18. The oral product of claim 17, wherein the gum is gum arabic.

19. The oral product of claim 1, further comprising an additive selected from the group consisting of flavorants, sweeteners, additional binders, emulsifiers, disintegration aids, humectants, salts, and mixtures thereof.

20. The oral product of claim 1, further comprising a buffering agent and/or a pH adjuster in an amount sufficient to adjust the pH of the oral product to be in the range of about 5.0 to about 7.0.

21. The oral product of claim 1, wherein the oral product has an outer coating coated thereon.

22. The oral product of claim 1, wherein the water content of the oral product is in the range of about 5% to about 20% by weight based on the total weight of the oral product.

23. The oral product of claim 22, wherein the water content of the oral product is in the range of about 5% to about 10% by weight based on the total weight of the oral product.

24. The oral product of claim 1, further comprising magnesium.

25. An oral product, comprising:
a sugar alcohol in an amount in the range of 25% to 45% by weight, based on the total weight of the composition;
a gum in an amount in the range of about 35% to about 55% by weight;
at least one active ingredient in an amount of about 10% or less by weight;
a humectant in an amount in the range of about 0.1% to about 5% by weight;
a salt in an amount in the range of about 0.1% to about 5% by weight;
a flavoring agent in an amount in the range of about 0.1% to about 5% by weight;
a water content in the range of about 5% to about 10% by weight; and
at least about 0.01% by weight of a sweetener,
wherein the oral product is free of a tobacco material.

26. The oral product of claim 25, further comprising magnesium.

27. A method of preparing an oral product, the method comprising:
mixing a gum and at least one active ingredient to provide a combined mixture thereof;
adding water, at least one additive, and at least one flavoring agent to the combined mixture to provide an aqueous mixture;
separately adding at least one sugar alcohol to the aqueous mixture to provide an oral composition;
heating the oral composition;
depositing the oral composition into a mold; and
curing the oral composition to provide an oral product in the form of a pastille,
wherein the oral product is free of a tobacco material.

28. The method of claim 27, wherein the gum is heated to a temperature in the range of about 40°° C. to about 80° C. prior to mixing with the at least one active ingredient.

29. The method of claim 27, wherein the at least one sugar alcohol is heated to a temperature in the range of about 160°° C. to about 190° C. and then optionally cooled to a temperature in the range of about 120° C. to about 150° C. prior to being added to the aqueous mixture.

30. The method of claim 27, wherein heating the oral composition comprises heating to a temperature in the range of about 60° C. to about 80° C.

31. The method of claim 27, wherein the at least on active ingredient is selected from the group consisting of a botanicals, nutraceuticals, stimulants, amino acids, vitamins, cannabinoids, cannabimimetics, terpenes, and combinations thereof.

32. The method of claim 27, wherein the at least one sugar alcohol is selected from the group consisting of erythritol, arabitol, ribitol, isomalt, maltitol, dulcitol, iditol, mannitol, xylitol, lactitol, sorbitol, and combinations thereof.

33. The method of claim 27, wherein the at least one additive is selected from the group consisting of flavorants, sweeteners, additional binders, emulsifiers, disintegration aids, humectants, salts, and mixtures thereof.

34. An oral product, the oral product comprising an active ingredient in an amount of 10 weight percent or less, a sugar substitute in an amount of at least about 80 weight percent; and a sugar alcohol syrup, the oral product being in the form of a lozenge, wherein the oral product is free of a tobacco material.

35. The oral product of claim 34, wherein the at least one active ingredient is selected from the group consisting of a botanicals, nutraceuticals, stimulants, amino acids, vitamins, cannabinoids, cannabimimetics, terpenes, and combinations thereof.

36. The oral product of claim 35, wherein the at least one active ingredient is selected from the group consisting of caffeine, taurine, GABA, theanine, tryptophan, vitamin B6, vitamin B12, vitamin C, lemon balm extract, ginseng, citicoline, sunflower lecithin, and combinations thereof.

37. The oral product of claim 36, wherein the at least one active ingredient comprises a combination of caffeine, taurine, and ascorbic acid.

38. The oral product of claim 37, wherein the caffeine is present in an amount of about 2% to about 4% by weight, the taurine is present in an amount of about 2% to about 4% by weight, and the ascorbic acid is present in an amount of about 1% to about 3% by weight, based on the total weight of the product.

39. The oral product of claim 36, wherein the at least one active ingredient comprises theanine, gamma-aminobutyric acid, and optionally lemon balm.

40. The oral product of claim 39, wherein the theanine is present in an amount of about 2% to about 4% by weight, the gamma-aminobutyric acid is present in an amount of about 2% to about 4% by weight, and the lemon balm is present in an amount of about 1% to about 3% by weight, based on the total weight of the product.

41. The oral product of claim 36, wherein the at least one active ingredient comprises caffeine, theanine, and optionally ginseng.

42. The oral product of claim 41, wherein the caffeine is present in an amount of about 2% to about 4%, the theanine is present in an amount of about 2% to about 4% by weight, and the ginseng is present in an amount of about 0.1% to about 1% by weight, based on the total weight of the product.

43. The oral product of claim 36, wherein the at least one active ingredient comprises:
theanine;
theanine and tryptophan; or
theanine and vitamin B6, vitamin B12, or both.

44. The oral product of claim 43, comprising theanine and one or both of vitamins B6 and vitamin B12.

45. The oral product of claim 34, wherein the at least one active ingredient is present in an amount in the range of about 6% to about 8% by weight based on the total weight of the product.

46. The oral product of claim 34, wherein the oral product is free of nicotine or a nicotine-derived component.

47. The oral product of claim 34, wherein the sugar substitute is a non-hygroscopic sugar alcohol capable of forming a glassy matrix.

48. The oral product of claim 47, wherein the sugar substitute is isomalt.

49. The oral product of claim 34, wherein the sugar substitute is present in an amount of at least about 85 weight percent.

50. The oral product of claim 49, wherein the sugar substitute is present in an amount of at least about 90 weight percent.

51. The oral product of claim 50, wherein the sugar substitute is present in an amount of at least about 95 weight percent.

52. The oral product of claim 34, wherein the sugar alcohol syrup is maltitol syrup.

53. The oral product of claim 34, further comprising an additive selected from the group consisting of flavorants, sweeteners, additional filler components, emulsifiers, disintegration aids, humectants, salts, and mixtures thereof.

54. The oral product of claim 34, further comprising a buffering agent and/or a pH adjuster in an amount sufficient to adjust the pH of the oral product to be in the range of about 5.0 to about 7.0.

55. The oral product of claim 34, wherein the water content of the oral product is in the range of about 0.1 weight percent to about 5 weight percent based on the total weight of the oral product.

56. The oral product of claim 34, further comprising magnesium.

* * * * *